(12) United States Patent
Li

(10) Patent No.: US 12,158,140 B2
(45) Date of Patent: Dec. 3, 2024

(54) HOUSEHOLD ELECTRIC APPLIANCE WITH HIGH/LOW-PRESSURE FUNCTION

(71) Applicant: Shiqing Li, Xintai (CN)

(72) Inventor: Shiqing Li, Xintai (CN)

(73) Assignee: Shiqing Li, Xintai (CN)

( * ) Notice: Subject to any disclaimer, the term of this patent is extended or adjusted under 35 U.S.C. 154(b) by 872 days.

(21) Appl. No.: 17/289,792

(22) PCT Filed: Oct. 30, 2019

(86) PCT No.: PCT/CN2019/000202
§ 371 (c)(1),
(2) Date: Apr. 29, 2021

(87) PCT Pub. No.: WO2020/087768
PCT Pub. Date: May 7, 2020

(65) Prior Publication Data
US 2021/0396220 A1    Dec. 23, 2021

(30) Foreign Application Priority Data

Oct. 31, 2018   (CN) .......................... 201811323062.0
Oct. 31, 2018   (CN) ......................... 201811323064.X
(Continued)

(51) Int. Cl.
*F16K 15/03*   (2006.01)
*A23L 3/015*   (2006.01)
(Continued)

(52) U.S. Cl.
CPC ............ *F04B 39/10* (2013.01); *A23L 3/0155* (2013.01); *A47L 15/4263* (2013.01); *A47L 23/02* (2013.01);
(Continued)

(58) Field of Classification Search
CPC .... F04B 39/10; F04B 39/0005; F16K 15/033; F25D 17/045
See application file for complete search history.

(56) References Cited

U.S. PATENT DOCUMENTS

2003/0223884 A1   12/2003  Hirota
2008/0257086 A1*  10/2008  Noritake .................. H02K 7/06
                                                                 74/422
(Continued)

FOREIGN PATENT DOCUMENTS

CN          103041416 A       4/2013
CN          204107292 U       1/2015
(Continued)

OTHER PUBLICATIONS

European Search Report for PCT Application No. PCT/CN2019/000202, mailed Jul. 18, 2022.
(Continued)

*Primary Examiner* — P. Macade Nichols
(74) *Attorney, Agent, or Firm* — Andrus Intellectual Property Law, LLP

(57) ABSTRACT

Provided a household electric appliance with a high/low-pressure function, and the household electric appliance with a high/low-pressure function includes a high/low-pressure forming apparatus, where the high/low-pressure forming apparatus includes a movement apparatus, a pressure forming rod, a pressure forming body, a pressure forming shell and a valve, and the valve includes a pressure suction valve and a pressurization valve. A pressure-resistant shell, a build-in groove, a sealing apparatus and a pressure-resistant build-in door are disposed on a device on a high-pressure compartment or a low-pressure compartment of the household electric appliance. The high-pressure compartment or the low-pressure compartment of the household electric appliance with the high/low-pressure function is integrally
(Continued)

provided with or coupled with the high/low-pressure forming apparatus through a high/low-pressure control valve and a pipe.

17 Claims, 12 Drawing Sheets

(30) Foreign Application Priority Data

| Oct. 31, 2018 | (CN) | 201811323065.4 |
|---|---|---|
| Oct. 31, 2018 | (CN) | 201811323121.4 |
| Oct. 31, 2018 | (CN) | 201811323143.0 |
| Oct. 31, 2018 | (CN) | 201811323144.5 |
| Oct. 31, 2018 | (CN) | 201811323169.5 |
| Oct. 30, 2019 | (CN) | 201911040619.4 |

(51) Int. Cl.
*A47L 15/42* (2006.01)
*A47L 23/02* (2006.01)
*A61L 2/02* (2006.01)
*D06F 39/14* (2006.01)
*F04B 39/00* (2006.01)
*F04B 39/10* (2006.01)
*F25D 17/04* (2006.01)

(52) U.S. Cl.
CPC ............... *A61L 2/02* (2013.01); *D06F 39/14* (2013.01); *F04B 39/0005* (2013.01); *F16K 15/033* (2013.01); *F25D 17/045* (2013.01)

(56) References Cited

U.S. PATENT DOCUMENTS

| 2009/0028723 A1* | 1/2009 | Wallis ............... F04B 49/225 |
| | | 417/295 |
| 2012/0192583 A1 | 8/2012 | Lifson et al. |
| 2014/0112812 A1 | 4/2014 | Takemi |
| 2015/0219085 A1* | 8/2015 | Yamaoka ............ F04B 39/1066 |
| | | 417/312 |
| 2017/0248132 A1 | 8/2017 | Chou |
| 2017/0335837 A1 | 11/2017 | Ventrapragada |

FOREIGN PATENT DOCUMENTS

| CN | 208222370 U | 12/2018 |
| EP | 1813803 A1 | 8/2007 |

OTHER PUBLICATIONS

International Search Report for PCT Application No. PCT/CN2019/000202, mailed Feb. 1, 2021.

* cited by examiner

HOUSEHOLD ELECTRIC APPLIANCE WITH HIGH/LOW-PRESSURE FUNCTION

CROSS-REFERENCE TO RELATED APPLICATION

This is a National stage application, filed under 37 U.S.C. 371, of International Patent Application NO. PCT/CN2019/000202, filed on Oct. 30, 2019, which is based on and claims priority to Chinese patent applications No. 201811323065.4, 201811323121.4, 201811323064.X, 201811323144.5, 201811323062.0, 201811323169.5 and 201811323143.0 filed on Oct. 31, 2018 and Chinese patent application No. 201911040619.4 filed on Oct. 30, 2019, disclosure of which are incorporated herein by reference in their entireties.

TECHNICAL FIELD

The present disclosure relates to a household electric appliance with a high/low-pressure function, and a high/low-pressure forming apparatus is configured to manufacture a high-pressure space or a low-pressure space.

BACKGROUND

At present, in order to vacuumize or increase pressure, it is difficult to unify a device on the one hand, and on the other hand, a pressure difference is too small and the efficiency is too low, which cannot adapt the demands of rapidly forming a low pressure or a high pressure and a relatively large pressure difference.

SUMMARY

The present disclosure is provided in view of the above problems and aims at providing a safety high/low-pressure forming apparatus, which can manufacture a low-pressure space environment or a high-pressure space environment in a fast and energy-efficient manner.

To achieve the preceding object, the present disclosure provides the solutions described below.

A household electric appliance with a high/low-pressure function is provided with a high/low-pressure forming apparatus and includes the high/low-pressure forming apparatus, where the high/low-pressure forming apparatus includes a movement apparatus, a pressure forming rod, a pressure forming body, a pressure forming shell and a valve, where the valve includes a pressure suction valve and a pressurization valve, and the high/low-pressure forming apparatus is a device for manufacturing a high-pressure compartment or a low-pressure compartment of the household electric appliance with the high/low-pressure function.

An outer periphery of a bottom of the pressure forming shell of the high/low-pressure forming apparatus is provided with the pressurization valve for manufacturing a pressure higher than an atmospheric pressure and a pressure suction valve for manufacturing a pressure lower than an atmospheric pressure.

The high/low-pressure forming apparatus is disposed on the household electric appliance with the high/low-pressure function, and the pressure forming shell is disposed on the high/low-pressure forming apparatus, wherein an inner side of the pressure forming shell is provided with one pressure forming body which reciprocates axially along a hole wall in the pressure forming shell, the pressure forming body is provided with one pressure forming rod in a movable fit manner, the other end of the one pressure forming rod is disposed together with the transmission apparatus in the movable fit manner, and a transmission apparatus is coupled with a power apparatus.

the pressure forming body axially reciprocates along the hole wall in the pressure forming shell, and when the pressure forming body reciprocates to a position where space between the pressure forming body in the pressure forming shell and a bottom cover of the pressure forming shell reaches the maximum and contains maximum amount of gas, the pressure forming body compresses space of internal gas to form a high pressure, or when the pressure forming body reciprocates to a position where space between the pressure forming body in the pressure forming shell and a bottom cover of the pressure forming shell reaches the minimum and contains minimum amount of gas, the pressure forming body expands space of internal gas to form a low-pressure A household electric appliance with a high/low-pressure function is provided with a pressure-resistant apparatus and a safety door and includes a high-pressure compartment or a low-pressure compartment formed in a pressure-resistant shell of the household electric appliance with the high/low-pressure function through adjusting high-pressure gas generated by a high/low pressure forming apparatus of the household electric appliance or a low-pressure pumped by a high/low pressure forming apparatus of the household electric appliance or low-pressure gas via a high/low-pressure control valve, where a pressure-resistant shell is provided with a built-in groove, a sealing apparatus and a pressure-resistant built-in door.

The pressure-resistant shell is disposed on the household electric appliance with the high/low-pressure function.

An inner side of the pressure-resistant shell is provided with the built-in groove, a pressure-resistant sealing apparatus is disposed in the built-in groove, and a pressure-resistant built-in door is disposed in the built-in groove via the pressure-resistant sealing apparatus.

An outer end of a side of the built-in groove is integrally provided with an opening on the pressure-resistant shell, and the pressure-resistant built-in door is completely pushed into a sealing state in the built-in groove via the opening of the pressure-resistant shell, and the pressure-resistant shell forms the high-pressure compartment or the low-pressure compartment through a pressurization apparatus or a pressure suction apparatus; or the pressure-resistant built-in door continues to move outward along a groove-shaped opening in the built-in groove to an open state to take out articles in the pressure-resistant shell, that is, the high-pressure compartment or the low-pressure compartment.

Preferably, the pressure suction valve or the pressurization valve of the high/low-pressure forming apparatus is respectively disposed together with the low-pressure compartment or the high-pressure compartment of the household electric appliance with the high/low-pressure function via a high/low-pressure control valve.

Preferably, the low-pressure compartment or the high-pressure compartment is disposed on the pressure-resistant shell of the household electric appliance with the high/low-pressure function.

Preferably, the low-pressure compartment or the high-pressure compartment of the household electric appliance with the high/low-pressure function includes one or more pressure-resistant shells.

Preferably, the household electric appliance with the high/low-pressure function is provided with one or more pressure-resistant shells.

Preferably, one or more built-in grooves are disposed on each pressure resistant shell.

Preferably, one or more sealing apparatuses are disposed in each built-in groove in one pressure-resistant shell.

Preferably, one or more sealing apparatuses and one or more pressure-resistant built-in doors are disposed in each of built-in groove in one pressure-resistant shell.

Preferably, one or more transparency inspection windows are disposed on one or more pressure-resistant built-in doors 35 in one pressure-resistant shell.

Preferable, one or more groove-shaped openings are disposed on one pressure-resistant shell.

Preferably, one or more pressure-resistant built-in doors are disposed in door frames of one or more groove-shaped openings of one pressure resistant shell.

Preferably, one or more pressure-regulating grooves are disposed on one or more built-in grooves of one pressure resistant shell.

A household electric appliance with the high/low-pressure function includes a high-pressure compartment or a low-pressure compartment, where a high/low-pressure control valve disposed on the high-pressure compartment or the low-pressure compartment includes a valve shell, a valve body and a valve deck.

The high-pressure compartment or the low-pressure compartment of the household electric appliance with the high/low-pressure function is provided with the high/low-pressure forming apparatus via a high/low-pressure control valve, and the high/low-pressure control valve includes the valve shell, the valve body and the valve deck.

The valve shell is provided with a pressurization port, a pressure reduction port, an air filling port, an air evacuation port, a circulating air inlet and a circulating air outlet.

The valve body is provided with a three-way hole, a circulating air intake hole and a circulating air vent hole.

A upper part of the valve body is provided with a valve handle, the valve handle is coupled with a transmission apparatus, and the three-way hole cooperates with the pressurization port, the air filling port, the pressure reduction port and the air evacuation port to form a closing or opening fit for a high pressure or a low pressure.

The circulating air intake hole cooperates with the pressurization port via the circulating air inlet, or the circulating air vent hole cooperates with the pressure reduction port via the circulating air outlet.

Preferably, at least one or more three-way holes are disposed on a valve body of the high/low-pressure control valve.

Preferably, at least one or more cycle holes are disposed on a valve body of the high/low-pressure control valve.

Preferably, at least one or more pressurization ports, at least one or more cycle ports and at least one or more air outlets are disposed on a valve shell of the high/low-pressure control valve.

Preferably, at least one or more pressure reduction ports, at least one or more circulation ports and at least one or more air inlets are disposed on a valve shell of the high/low-pressure control valve.

Preferably, a sealing cover is disposed at the bottom of the valve shell of the high/low-pressure control valve.

Preferably, the bottom of the valve shell of the high/low-pressure control valve is provided with a lubrication hole, and the lubrication hole is sealed by a screw.

A household electric appliance with the high/low-pressure function includes a high/low-pressure forming apparatus, and the high/low-pressure forming apparatus includes a movement apparatus, a pressure forming rod, a pressure forming body, a pressure forming shell and a valve, where the valve includes a pressure suction valve and a pressurization valve, and the high/low-pressure forming apparatus is a device for manufacturing a high-pressure compartment or a low-pressure compartment.

The high/low-pressure forming apparatus is disposed on the household electric appliance with the high/low-pressure function, and two pressure forming shells are disposed on the high/low-pressure forming apparatus.

An inner side of each of the two pressure forming shells is provided with one pressure forming body which reciprocates axially along a hole wall in the each of the two pressure forming shells, one pressure forming rod is disposed on each pressure forming body in a movable fit manner, the other ends of two pressure forming rods are disposed together with a transmission apparatus in the movable fit manner, and the transmission apparatus is coupled with a power apparatus.

The pressure forming body axially reciprocates along the hole wall in the pressure forming shell, and when the pressure forming body reciprocates to a position where space between the pressure forming body in the pressure forming shell and a bottom cover of the pressure forming shell reaches the maximum and contains maximum amount of gas, the pressure forming body compresses space of internal gas to form a high pressure, or when the pressure forming body reciprocates to a position where space between the pressure forming body in the pressure forming shell and a bottom cover of the pressure forming shell reaches the minimum and contains minimum amount of gas, the pressure forming body expands space of internal gas to form a low pressure.

An outer periphery of a bottom of the each of the two pressure forming shells of the high/low-pressure forming apparatus is provided with the pressurization valve for manufacturing a pressure higher than an atmospheric pressure and a pressure suction valve for manufacturing the pressure lower than the atmospheric pressure.

A household electric appliance with a high/low-pressure function includes a high/low-pressure forming apparatus, and the high/low-pressure forming apparatus includes a movement apparatus, a pressure forming rod, a pressure forming body, a pressure forming shell and a valve, where the valve includes a pressure suction valve and a pressurization valve, and the high/low-pressure forming apparatus is a device for manufacturing a high-pressure compartment or a low-pressure compartment.

The high/low-pressure forming apparatus is disposed on the household electric appliance with the high/low-pressure function, and the pressurization valve for manufacturing a pressure higher than an atmospheric pressure and the pressure suction valve for manufacturing the pressure lower than the atmospheric pressure are disposed on the high/low-pressure forming apparatus.

A cavity of the pressure suction valve is provided with a pressure suction valve rotating body in a movable fit manner, a check valve is disposed in the pressure suction valve rotating body, the pressure suction valve rotating body is disposed in the cavity of the pressure suction valve in a movable fit manner, a cavity of the pressurization valve is provided with a pressurization valve rotating body in a movable fit manner, the check valve is disposed in the pressurization valve rotating body, and the pressurization valve rotating body is disposed in the cavity of the pressurization valve in the movable fit manner.

A top end of each of the pressure suction valve rotating body and the pressurization valve rotating body is provided with a rotating handle, and the rotating handle is coupled with a rotating apparatus.

A high/low-pressure forming apparatus includes a movement apparatus, a pressure forming rod, a pressure forming body, a pressure forming shell and a valve, where the valve includes a pressure suction valve and a pressurization valve, and the high/low-pressure forming apparatus is a device for manufacturing a high-pressure compartment or a low-pressure compartment.

The pressurization valve for manufacturing a pressure higher than an atmospheric pressure and the pressure suction valve for manufacturing the pressure lower than the atmospheric pressure are disposed on the high/low-pressure forming apparatus.

A cavity of the pressure suction valve of the high/low-pressure forming apparatus is provided with a pressure suction valve rotating body in a movable fit manner, a check valve is disposed in the pressure suction valve rotating body, the pressure suction valve rotating body is disposed in the cavity of the pressure suction valve in the movable fit manner, and a cavity of the pressurization valve is provided with a pressurization valve rotating body in a movable fit manner.

The check valve is disposed in the pressurization valve rotating body, and the pressurization valve rotating body is disposed in the cavity of the pressurization valve in the movable fit manner.

A top end of each of the pressure suction valve rotating body and the pressurization valve rotating body is provided with a rotating handle, and the rotating handle is coupled with a rotating apparatus.

Preferably, multiple pressure forming shells is disposed on the household electric appliance with the high/low-pressure function.

Two pressure forming bodies which reciprocate axially along a hole wall in the each of the plurality of pressure forming shells are disposed in each of the plurality of pressure forming shells, one pressure forming rod is disposed on the each of the two pressure forming bodies in the movable fit manner, one eccentric gear or one eccentric rod is disposed on two pressure forming rods in the movable fit manner, and the one eccentric gear or the one eccentric rod is disposed together with the power apparatus via the transmission apparatus.

Preferably, an outer periphery of a bottom of the pressure forming shell of the high/low-pressure forming apparatus is provided with the pressure suction valve and the pressurization valve, a rotating apparatus of the pressure suction valve and a rotating apparatus of the pressurization valve are intercoupled and coupled with the power apparatus via the transmission apparatus, the rotating handles are driven by the rotating apparatus of the pressure suction valve and the rotating apparatus of the pressurization valve, and rotations of the rotating handles drive the pressure suction valve rotating body and the pressurization valve rotating body to rotate a direction of the pressure suction valve rotating body and a direction of the pressurization valve rotating body and change a direction of an airflow movement, thereby switching a flow direction of a suctioning or outputting gas or fluid for the high pressure or the low pressure in a compartment of an external device coupled with the high/low-pressure apparatus.

Preferably, a rotating apparatus disposed on the pressure suction valve rotating handle and a rotating apparatus disposed on the pressurization valve rotating handle of the high/low pressure forming apparatus are disposed together via the transmission apparatus.

Preferably, the bottom of the pressure forming shell of the high/low-pressure forming apparatus is integrally closed or a sealing cover is disposed at the bottom of the pressure forming shell, the valve is disposed at the bottom of the pressure forming shell or the sealing cover, that is, the outer periphery of the bottom of the pressure forming shell, and the valve includes the pressure suction valve and the pressurization valve.

A refrigerator includes a high/low-pressure forming apparatus, a refrigerator pressure-resistant outer shell, a dry filter, a capillary tube, a refrigeration system, a refrigerator shell, a safety valve (restricting the maximum pressure and the minimum pressure), a refrigerator pressure-resistant inner shell, a refrigerator pressure-resistant door, a cold storage chamber and a freezing refrigerator system.

The cold storage chambers of various refrigeration devices such as the refrigerator achieve the purpose of fresh keeping of food and odor removal through reducing the activity of microbes at the low oxygen, low-pressure gas or fluid and low-temperature environment which is lower than the lower-pressure of the atmospheric pressure.

Various refrigeration devices such as the refrigerator are each integrally provided with or coupled with the high/low-pressure forming apparatus 1. The high/low-pressure forming apparatus 1 is integrally provided with or coupled with a pressurization valve 15 for manufacturing a pressure higher than an atmospheric pressure and a pressure suction valve 11 for manufacturing a pressure lower than the atmospheric pressure.

The pressure suction valve disposed on the high/low-pressure forming apparatus expels the gas in the cold storage chamber to form a low-pressure cold storage chamber in which the pressure in the cold storage chamber is lower than the external atmospheric pressure.

A refrigerator includes a high/low-pressure forming apparatus, a refrigerator pressure-resistant outer shell, a dry filter, a capillary tube, a refrigeration system, a refrigerator shell, a safety valve (restricting the maximum pressure and the minimum pressure), a refrigerator pressure-resistant inner shell, a pressure regulating valve, a refrigerator pressure-resistant door, a cold storage chamber and a freezing refrigerator system.

The cold storage chambers of various refrigeration equipment such as the refrigerator process and pickle the food and retain freshness of the food in a manner of high-pressure infiltration at the high-pressure and low-temperature environment higher than the atmospheric pressure.

Various refrigeration devices such as the refrigerator are each integrally provided with or coupled with the high/low-pressure forming apparatus 1. The high/low-pressure forming apparatus 1 is integrally provided with or coupled with a pressurization valve 15 for manufacturing a pressure higher than an atmospheric pressure and a pressure suction valve 11 for manufacturing a pressure lower than the atmospheric pressure.

The pressurization valve 15 disposed on the high/low-pressure forming apparatus increases the gas in the cold storage chamber to form a high-pressure cold storage chamber in which the pressure in the cold storage chamber is higher than the external atmospheric pressure.

A refrigerator includes a refrigeration system, a refrigerator shell and a high/low-pressure forming apparatus, where the high/low-pressure forming apparatus includes a movement apparatus, a pressure forming rod, a pressure forming body, a pressure forming shell and a valve, and the valve includes a pressure suction valve and a pressurization valve.

The cold storage chambers of various refrigeration devices such the refrigerator use a low-pressure for reducing the activity of microbes at the low oxygen, low-pressure gas or fluid and low-temperature environment which is lower than the lower-pressure of the atmospheric pressure, a low-pressure for pickling the food and retaining freshness of the food in a manner of high-pressure infiltration at the normal pressure and the high-pressure higher than the atmospheric pressure and process and retain freshness of the food and drug in a manner that the normal pressure and the high-pressure are changed circularly in a low-temperature condition.

Various refrigeration devices such as the refrigerator are each integrally provided with or coupled with the high/low-pressure forming apparatus.

The pressure suction valve of the high/low-pressure forming apparatus is coupled with the pipe through a control valve and expels the gas in the cold storage chamber to form a space in which the pressure in the cold storage chamber is lower than the external atmospheric pressure; or the pressurization valve is coupled with the pipe through a control valve and increases the gas in the cold storage chamber to form a space in which the pressure in the cold storage chamber is higher than the external atmospheric pressure.

The cold storage chamber of the refrigerator processes and retains freshness of the food and drug in a cycle changing environment of the low-pressure and the high-pressure under the low-temperature condition.

A variable-pressure washing machine includes a variable-pressure washing machine shell, a sealing door and a washing chamber, where a water inlet valve, a drain valve and a breather valve are disposed on the washing chamber, and a high/low-pressure forming apparatus is disposed on the variable-pressure washing machine shell. A high/low-pressure forming apparatus includes a movement apparatus, a pressure forming rod, a pressure forming body, a pressure forming shell and a valve, where the valve includes a pressure suction valve and a pressurization valve.

The variable-pressure washing machine washes clothes in a manner of intensively decomposing and separating dirt and oil dirt on the clothes in a low-pressure environment of which a pressure is lower than the atmospheric pressure in the washing chamber.

The high/low-pressure forming apparatus is disposed on the variable-pressure washing machine, the high/low-pressure forming apparatus may generate a low-pressure lower than the atmospheric pressure, and a pressurization valve for manufacturing a pressure higher than the atmospheric pressure and a pressure suction valve for manufacturing a pressure lower than the atmospheric pressure are disposed on the high/low-pressure forming apparatus.

The washing chamber of the variable-pressure washing machine is coupled with the pressure suction valve via a high/low-pressure control valve and a pipe, and the pressure suction valve expels the gas or the fluid in the washing chamber to form a low-pressure washing chamber in which a pressure in the washing chamber is lower than the pressure of the external atmospheric environment.

A variable-pressure washing machine includes a variable-pressure washing machine shell, a sealing door and a washing chamber, where a water inlet valve, a drain valve and a breather valve are disposed on the washing chamber, and a high/low-pressure forming apparatus is disposed on the variable-pressure washing machine shell. A high/low-pressure forming apparatus includes a movement apparatus, a pressure forming rod, a pressure forming body, a pressure forming shell and a valve, where the valve includes a pressure suction valve and a pressurization valve.

The variable-pressure washing machine washes clothes by permeating into the dirt and the oil dirt on the clothes in a manner of strongly permeating laundry detergent in a high-pressure environment whose pressure is higher than the atmospheric pressure in the washing machine.

The high/low-pressure forming apparatus is disposed on the variable-pressure washing machine, the high/low-pressure forming apparatus may generate a high-pressure higher than the atmospheric pressure, and a pressurization valve for manufacturing a pressure higher than the atmospheric pressure and a pressure suction valve for manufacturing a pressure lower than the atmospheric pressure are disposed on the high/low-pressure forming apparatus.

The washing chamber of the variable-pressure washing machine is coupled with the pressurization valve via a high/low-pressure control valve and a pipe, and the pressurization valve increases the gas or the fluid in the washing chamber to form a high-pressure washing chamber in which a pressure in the washing chamber is higher than the pressure of the external atmospheric environment.

A variable-pressure washing machine includes a variable-pressure washing machine shell, a sealing door and a washing chamber, where a water inlet valve, a drain valve and a breather valve are disposed on the washing chamber, and a high/low-pressure forming apparatus is disposed on the variable-pressure washing machine shell. A high/low-pressure forming apparatus includes a movement apparatus, a pressure forming rod, a pressure forming body, a pressure forming shell and a valve, where the valve includes a pressure suction valve and a pressurization valve.

The variable-pressure washing machine washes clothes in a manner of decomposing and separating dirt and oil dirt on the clothes in a low pressure lower than the atmospheric pressure, washes the clothes by permeating into the dirt and the oil dirt on the clothes in a manner of strongly permeating laundry detergent in a high-pressure environment whose pressure is higher than the atmospheric pressure, and washes the clothes in a manner that the normal pressure and the low pressure are changed circularly.

The high/low-pressure forming apparatus is disposed on the variable-pressure washing machine, and the pressurization valve and the pressure suction valve are disposed on the washing chamber. The pressure suction valve expels the gas or fluid in the washing chamber to form the pressure in the washing chamber lower than the external atmospheric pressure, and the pressurization valve increases the gas or fluid in the washing chamber to form the pressure in the washing chamber higher than the external atmospheric pressure for changing circularly.

A safety valve is disposed on the washing chamber of the variable-pressure washing machine and coupled with the atmospheric environment.

A deodorizing and perfuming machine includes a deodorizing and perfuming machine shell, a safety door, a clothes treatment chamber, a sealing door and a high/low-pressure forming apparatus, where the high/low-pressure forming apparatus includes a movement apparatus, a pressure forming rod, a pressure forming body, a pressure forming shell and a valve, and the valve includes a pressure suction valve and a pressurization valve.

The deodorizing and perfuming machine is provided with a sealed clothes treatment chamber, and the clothes treatment chamber adopts a low-pressure lower than an atmospheric pressure to decompose and separate sweat stain odor and dehumidify.

The high/low-pressure forming apparatus is disposed on the deodorizing and perfuming machine, the high/low-pressure forming apparatus may generate a low-pressure lower than the atmospheric pressure, and a pressurization valve for manufacturing a pressure higher than the atmospheric pressure and a pressure suction valve for manufacturing a pressure lower than the atmospheric pressure are disposed on the high/low-pressure forming apparatus.

The clothes treatment chamber of the deodorizing and perfuming machine is coupled with the pressure suction valve via a high/low-pressure control valve and a pipe, and the pressure suction valve expels the gas or the fluid in the clothes treatment chamber to form a low-pressure clothes treatment chamber in which a pressure in the clothes treatment chamber is lower than the pressure of the external atmospheric environment.

A deodorizing and perfuming machine includes a deodorizing and perfuming machine shell, a safety door, a clothes treatment chamber, a sealing door and a high/low-pressure forming apparatus, where the high/low-pressure forming apparatus includes a movement apparatus, a pressure forming rod, a pressure forming body, a pressure forming shell and a valve, and the valve includes a pressure suction valve and a pressurization valve.

The deodorizing and perfuming machine is provided with a sealed clothes treatment chamber, and the clothes treatment chamber uses a high-pressure higher than an atmospheric pressure in the clothes treatment chamber to highly permeate a perfume and a drug into clothes.

The high/low-pressure forming apparatus is disposed on the deodorizing and perfuming machine, the high/low-pressure forming apparatus may generate a high-pressure higher than the atmospheric pressure, and a pressurization valve for manufacturing a pressure higher than the atmospheric pressure and a pressure suction valve for manufacturing a pressure lower than the atmospheric pressure are disposed on the high/low-pressure forming apparatus.

The clothes treatment chamber of the deodorizing and perfuming machine is coupled with the pressurization valve via a high/low-pressure control valve and a pipe, and the pressure suction valve increases the gas or the fluid in the clothes treatment chamber to form a high-pressure clothes treatment chamber in which a pressure in the clothes treatment chamber is higher than the pressure of the external atmospheric environment.

A deodorizing and perfuming machine includes a deodorizing and perfuming machine shell, a safety door, a clothes treatment chamber, a sealing door and a high/low-pressure forming apparatus, where the high/low-pressure forming apparatus includes a movement apparatus, a pressure forming rod, a pressure forming body, a pressure forming shell and a valve, and the valve includes a pressure suction valve and a pressurization valve.

The clothes treatment chamber of the deodorizing and perfuming machine uses a low-pressure lower than the atmospheric pressure to decompose and separate odor and dehumidify, carries out normal pressure regulation, or uses a high-pressure higher than the atmospheric pressure to enhance a perfume and a drug to highly permeate into clothes, and treats the clothes in a manner that the low pressure, the normal pressure and the high-pressure are changed circularly.

The high/low-pressure forming apparatus is disposed on the deodorizing and perfuming machine, and the pressurization valve and the pressure suction valve are disposed on the high/low-pressure forming apparatus. The pressure suction valve expels the gas or fluid in the clothes treatment chamber to form the pressure in the clothes treatment chamber lower than the external atmospheric pressure, and the pressurization valve increases the gas or fluid in the clothes treatment chamber to form the pressure in the clothes treatment chamber higher than the external atmospheric pressure for changing circularly.

The pressure suction valve and the pressurization valve are respectively coupled with the atmospheric environment outside the deodorizing and perfuming machine through a control valve and a pipe.

A pickling machine includes a high/low-pressure forming apparatus, a pickling machine shell, a safety valve (restricting the maximum pressure and the minimum pressure), a pressure regulating valve, a pickling machine pressure-resistant door, a processing chamber and a valve, where the valve includes a pressure suction valve and a pressurization valve.

The processing chamber of the pickling machine dispels microbes and mold in the low oxygen of the low-pressure which is lower than the lower-pressure of the atmospheric pressure, low-pressure gas environment to achieve the purpose of removing odor and mold for the food and drug and avoid nutrient loss caused by excessive cleaning.

The high/low-pressure forming apparatus disposed on the pickling machine, and a pressurization valve 15 for manufacturing a pressure higher than an atmospheric pressure and a pressure suction valve for manufacturing the pressure lower than the atmospheric pressure are disposed on the high/low-pressure forming apparatus.

The pressure suction valve disposed on the high/low-pressure forming apparatus via the pipe expels the gas in the processing chamber of the pickling machine to form a low-pressure processing chamber in which the pressure in the processing chamber is lower than the external atmospheric pressure.

A pickling machine includes a high/low-pressure forming apparatus, a pickling machine shell, a safety valve (restricting the maximum pressure and the minimum pressure), a pressure regulating valve, a pickling machine pressure-resistant door, a processing chamber and a valve, where the valve includes a pressure suction valve and a pressurization valve.

The processing chamber, in which the high-pressure is higher than the atmospheric pressure, of the pickling machine, processes the food and drug in a high-pressure infiltration pickling manner.

The high/low-pressure forming apparatus is disposed on the pickling machine, and a pressurization valve 15 for manufacturing a pressure higher than an atmospheric pressure and a pressure suction valve for manufacturing the pressure lower than the atmospheric pressure are disposed on the high/low-pressure forming apparatus.

The pressurization valve 15 disposed on the high/low-pressure forming apparatus via the pipe increases the gas in the processing chamber to form a high-pressure processing chamber in which the pressure in the processing chamber is higher than the external atmospheric pressure.

A pickling machine includes a pickling machine shell and a high/low-pressure forming apparatus, where the high/low-pressure forming apparatus includes a movement apparatus, a pressure forming rod, a pressure forming body, a pressure forming shell and a valve, and the valve includes a pressure suction valve and a pressurization valve.

The processing chamber of the pickling machine uses a low oxygen, a low-pressure air environment which is lower than the lower-pressure of the atmospheric pressure to discharge odor and microbes on the food and drug, carries out normal pressure regulation, or uses a low-pressure for infiltrating and pickling the food and drug in a manner of high-pressure infiltration at the high-pressure higher than the atmospheric pressure and processes and retains freshness of the food and drug in a manner that the normal pressure and the high-pressure are changed circularly.

The high/low-pressure forming apparatus is disposed on the processing chamber of the pickling machine via the pipe, and a pressurization valve and a pressure suction valve are disposed on the high/low-pressure forming apparatus.

The pressure suction valve of the high/low-pressure forming apparatus expels the gas in the processing chamber to form the pressure in the processing chamber which is lower than the external atmospheric pressure; or the pressurization valve increases the gas in the processing chamber to form the pressure in the processing chamber which is higher than the external atmospheric pressure.

The pressure suction valve of the high/low-pressure forming apparatus is coupled with the pipe through a control valve and expels the gas in the processing chamber to form the pressure in the processing chamber which is lower than the external atmospheric pressure; or the pressurization valve is coupled with the pipe through a control valve and increases the gas in the processing chamber to form the pressure in the processing chamber which is higher than the external atmospheric pressure.

A variable-pressure dish-washing machine includes a variable-pressure dish-washing machine shell, a pantry, a sealing door and a high/low-pressure forming apparatus, where the high/low-pressure forming apparatus includes a movement apparatus, a pressure forming rod, a pressure forming body, a pressure forming shell and a valve, and the valve includes a pressure suction valve and a pressurization valve.

The variable-pressure dish-washing machine washes tablewares in a manner of intensively decomposing and separating dirt and oil dirt on the tablewares in a low-pressure environment of which a pressure is lower than the atmospheric pressure in the pantry.

The high/low-pressure forming apparatus is disposed on the variable-pressure dish-washing machine, the high/low-pressure forming apparatus may generate a low-pressure lower than the atmospheric pressure, and a pressurization valve for manufacturing a pressure higher than the atmospheric pressure and a pressure suction valve for manufacturing a pressure lower than the atmospheric pressure are disposed on the high/low-pressure forming apparatus.

A dish-washing chamber of the variable-pressure dish-washing machine is coupled with the pressure suction valve via a high/low-pressure control valve and a pipe, and the pressure suction valve expels the gas or the fluid in the dish-washing chamber to form a low-pressure pantry in which a pressure in the dish-washing chamber is lower than the pressure of the external atmospheric environment.

A variable-pressure dish-washing machine includes a variable-pressure dish-washing machine shell, a pantry, a sealing door and a high/low-pressure forming apparatus, where the high/low-pressure forming apparatus includes a movement apparatus, a pressure forming rod, a pressure forming body, a pressure forming shell and a valve, and the valve includes a pressure suction valve and a pressurization valve.

The variable-pressure washing machine washes tablewares by permeating into the dirt and the oil dirt on the tablewares in a manner of strongly permeating detergent in a high-pressure environment whose pressure is higher than the atmospheric pressure in the pantry.

The high/low-pressure forming apparatus is disposed on the variable-pressure dish-washing machine, the high/low-pressure forming apparatus may generate a high-pressure higher than the atmospheric pressure, and a pressurization valve for manufacturing a pressure higher than the atmospheric pressure and a pressure suction valve for manufacturing a pressure lower than the atmospheric pressure are disposed on the high/low-pressure forming apparatus.

A dish-washing chamber of the variable-pressure dish-washing machine is coupled with the pressurization valve via a high/low-pressure control valve and a pipe, and the pressurization valve increases the gas or the fluid in the dish-washing chamber to form a high-pressure pantry in which a pressure in the dish-washing chamber is higher than the pressure of the external atmospheric environment.

A variable-pressure dish-washing machine includes a variable-pressure dish-washing machine shell, a sealing door, a pantry and a high/low-pressure forming apparatus, where the high/low-pressure forming apparatus includes a movement apparatus, a pressure forming rod, a pressure forming body, a pressure forming shell and a valve, and the valve includes a pressure suction valve and a pressurization valve.

The pantry of the variable-pressure dish-washing machine washes tablewares in a manner of decomposing and separating dirt and oil dirt on the tablewares in a low pressure lower than the atmospheric pressure, washes the tablewares by permeating into the dirt and the oil dirt on the clothes in a manner of strongly permeating detergent in a high-pressure environment whose pressure is higher than the atmospheric pressure, and washes the tablewares in a manner that the normal pressure and the low pressure are changed circularly.

The high/low-pressure forming apparatus is disposed on the variable-pressure dish-washing machine, and the pressurization valve and the pressure suction valve are disposed on the high/low-pressure forming apparatus. The pressure suction valve expels the gas or fluid in the dish-washing chamber to form the pressure in the dish-washing chamber lower than the external atmospheric pressure, and the pressurization valve increases the gas or fluid in the dish-washing chamber to form the pressure in the dish-washing chamber higher than the external atmospheric pressure for changing circularly.

The pressure suction valve and the pressurization valve are respectively coupled with the atmospheric environment or the dish-washing chamber of the variable-pressure dish-washing machine through a control valve and a pipe.

A footwear foot-care machine includes a footwear foot-care machine shell, a sealing door, a high/low-pressure forming apparatus and a footwear chamber, where the high/low-pressure forming apparatus includes a movement apparatus, a pressure forming rod, a pressure forming body, a pressure forming shell and a valve, and the valve includes a pressure suction valve and a pressurization valve.

The sealed footwear chamber is disposed on the footwear foot-care machine, and sweat stain odor on footwear is decomposed and separated in the footwear chamber in a reinforced mode through a low-pressure lower than an atmospheric pressure in the footwear chamber.

A vibration apparatus is disposed in the footwear chamber of the footwear foot-care machine, and vibration generated by the vibration apparatus promotes the scrubbing solution and footwear to fully wash and decompose dirt and oil dirt, and then discharge the scrubbing solution from the footwear chamber.

The high/low-pressure forming apparatus is disposed on the footwear foot-care machine, the high/low-pressure forming apparatus may generate a low-pressure lower than the atmospheric pressure, and a pressurization valve for manufacturing a pressure higher than the atmospheric pressure and a pressure suction valve for manufacturing a pressure lower than the atmospheric pressure are disposed on the high/low-pressure forming apparatus.

The footwear chamber of the footwear foot-care machine is coupled with the pressure suction valve via a high/low-pressure control valve and a pipe, and the pressure suction valve expels the gas or the fluid in the footwear chamber to form a low-pressure footwear chamber in which a pressure in the footwear chamber is lower than the pressure of the external atmospheric environment.

A footwear foot-care machine includes a footwear foot-care machine shell, a footwear chamber, a sealing door and a high/low-pressure forming apparatus, where the high/low-pressure forming apparatus includes a movement apparatus, a pressure forming rod, a pressure forming body, a pressure forming shell and a valve, and the valve includes a pressure suction valve and a pressurization valve.

A sealed footwear chamber is disposed on the footwear foot-care machine, and the footwear chamber uses a high-pressure higher than an atmospheric pressure in the footwear chamber to highly permeate a perfume and a drug into the footwear.

The high/low-pressure forming apparatus is disposed on the footwear foot-care machine, the high/low-pressure forming apparatus may generate a high-pressure higher than the atmospheric pressure, and a pressurization valve for manufacturing a pressure higher than the atmospheric pressure and a pressure suction valve for manufacturing a pressure lower than the atmospheric pressure are disposed on the high/low-pressure forming apparatus.

The footwear chamber of the footwear foot-care machine is coupled with the pressurization valve via a high/low-pressure control valve and a pipe, and the pressurization valve increases the gas or the fluid in the footwear chamber to form a high-pressure footwear chamber in which a pressure in the footwear chamber is higher than the pressure of the external atmospheric environment.

A footwear foot-care machine includes a footwear foot-care machine shell, a sealing door, a footwear chamber and a high/low-pressure forming apparatus, where the high/low-pressure forming apparatus includes a movement apparatus, a pressure forming rod, a pressure forming body, a pressure forming shell and a valve, and the valve includes a pressure suction valve and a pressurization valve.

The footwear foot-care machine processes the footwear in a manner of decomposing and separating sweat stain odor on the footwear in a low pressure lower than the atmospheric pressure, processes the footwear by permeating into the sweat stain odor on the footwear in a manner of strongly permeating detergent in a high-pressure environment whose pressure is higher than the atmospheric pressure, and processes the footwear in a manner that the normal pressure and the low pressure are changed circularly.

The high/low-pressure forming apparatus is disposed on the footwear foot-care machine, and the pressurization valve and the pressure suction valve are disposed on the high/low-pressure forming apparatus. The pressure suction valve expels the gas or fluid in the footwear chamber to form the pressure in the footwear chamber lower than the external atmospheric pressure, and the pressurization valve increases the gas or fluid in the footwear chamber to form the pressure in the footwear chamber higher than the external atmospheric pressure for changing circularly.

The pressure suction valve and the pressurization valve are respectively coupled with the atmospheric environment of the footwear foot-care machine through a control valve and a pipe.

Preferably, the high/low-pressure forming apparatus forms the mutual conversion of the high-pressure forming function or the low-pressure forming function of the high/low-pressure forming apparatus through the rotation reverse of the valve rotating body.

Preferably, the movement apparatus is disposed on the high/low-pressure forming apparatus of the household electric appliance with the high/low-pressure function, where the movement apparatus is driven by a motor or an engine to drive a speed change mechanism or the pulley or a sprocket to drive an eccentric gear to rotate, the eccentric gear is disposed together with the pressure forming rod in a movable fit manner, and the pressure forming body and the pressure forming rod are disposed together in the movable fit manner to reciprocate along the pressure forming shell.

Preferably, the high/low-pressure forming apparatus of the household electric appliance with the high/low-pressure function refers to a gear pump or a vane pump or a plunger pump, or the pressurization valve and the pressure suction valve refer to the check valve or a plunger valve or a butterfly valve or a gate valve.

Preferably, when the pressure forming body axially reciprocates along the hole wall in the pressure forming shell to a position where space between the pressure forming body in the pressure forming shell and a bottom cover of the pressure forming shell reaches the maximum and contains maximum amount of gas, the pressure forming body compresses space of internal gas to form a high pressure, or when the pressure forming body axially reciprocates along the hole wall in the pressure forming shell to a position where to a position where space between the pressure forming body in the pressure forming shell and a bottom cover of the pressure forming shell reaches the minimum and contains minimum amount of gas, the pressure forming body expands space of internal gas to form a low pressure.

Preferably, the movement apparatus includes a power system and a drive system, where the power system includes a motor and an engine, and the drive system includes a gear drive or a speed change box drive or a pulley drive.

Preferably, the pressure forming shell is disposed on the high/low-pressure forming apparatus of the household electric appliance with the high/low pressure function, an outer periphery of a bottom of the pressure forming shell is provided with at least one pressure suction valve and at least one pressurization valve, and the at least one pressure suction valve or the at least one pressurization valve of the pressure forming shell of the high/low-pressure forming apparatus is provided with multiple cold storage chambers.

Preferably, a vibration apparatus capable of generating vibration is disposed on the cold storage chamber of the refrigerator and the cold storage chambers of various refrigeration devices, and the vibration apparatus may vibrate articles placed inside the cold storage chambers of the refrigeration devices.

Preferably, a high/low-pressure control valve is disposed on a pipe of the household electric appliance with the high/low-pressure function, and the high/low-pressure control valve is cooperated with the pressure suction valve and the pressurization valve to regulate an airflow direction.

Preferably, the vibration apparatus disposed on the cold storage chamber of the refrigerator and the cold storage chambers of various refrigeration devices refers to a mechanical vibration or an electronic vibration generated in a mechanical manner, or an electromagnetism vibration.

Preferably, the movement apparatus is disposed on the high/low-pressure forming apparatus, where the movement apparatus is driven by the motor to drive the speed change mechanism to drive the eccentric gear to rotate, the eccentric gear is disposed together with the pressure forming rod in a movable fit manner, and the pressure forming body and the pressure forming rod are disposed together in the movable fit manner to reciprocate along the pressure forming shell.

Preferably, the cold storage chamber of the refrigerator has a space with a low pressure or a space with a high-pressure.

Preferably, the valve is a check valve, the pressurization valve is a directional intake check valve, and the pressure suction valve is a directional exhaust check valve, or the check valve is rotated by a rotating body in a valve cavity to change the direction of fluid flow, and also known as a dual-direction check valve.

Preferably, a high-pressure anti-opening safety door is disposed on the household electric appliance with the high/low-pressure function, a high-pressure locking apparatus is disposed on a refrigerator safety door, and the high-pressure locking apparatus is locked by an inside high-pressure ejecting locating pin and is unlocked by a spring ejecting the locating pin under a normal pressure.

Preferably, the household electric appliance with the high/low-pressure function is provided with a microcomputer and a keyboard apparatus.

Preferably, the refrigerator safety valve is provided with high-pressure limiting apparatuses of an ultra-safe high-pressure vent and an ultra-safe low-pressure intake and low-pressure limiting apparatuses of an ultra-safe high-pressure vent and an ultra-safe low-pressure intake.

Preferably, the pressure suction valve of the household electric appliance with the high/low-pressure function and the pressurization valve of the household electric appliance with the high/low-pressure function are disposed together in a movable fit manner.

Preferably, the refrigerator uses a refrigeration system and a pressurization apparatus to cooperate and set up to manufacture a high-pressure freezing space to process the food.

Preferably, the household electric appliance with the high/low-pressure function is provided with a spice bottle or a drug bottle which is positioned and coupled with the cold storage chamber through the valve and the pipe.

Preferably, the outer periphery of the bottom of the pressure forming shell of the high/low-pressure forming apparatus of the household electric appliance with the high/low-pressure function or the bottom of the pressure forming shell is integrally a sealing cover, the valve is disposed at the bottom of the pressure forming shell or the sealing cover, and the valve includes the pressure suction valve and the pressurization valve.

The beneficial effects are described below.

Since the high/low-pressure forming apparatus includes a movement apparatus, a pressure forming rod, a pressure forming body, a pressure forming shell and a valve, where the valve includes a pressure suction valve and a pressurization valve, a high efficiency, high-speed, high/low-pressure forming apparatus for rapidly pumping and discharging gas or pressurizing gas is formed. The high/low-pressure forming apparatus has a simple structure, light weight, low power consumption, high efficiency, large pressure difference between the high pressure and the low pressure, can effectively manufacture the compartment with the low pressure or the high pressure of external device, and has widely application. Dirty gas and germs and molds are pumped into the atmosphere by utilizing the pressure reduction effect, which is beneficial to fresh keeping of food. Thus, the troublesome problem of cleaning the cold storage chamber of the refrigerator is solved, and the problem of processing the clothes is solved. Pickling food under the high-pressure is quick, which can effectively reduce toxic and harmful chemical components slowly produced in the pickling process. A pressure-resistant box body under the high pressure or the low-pressure environment is easy to manufacture, but a closed door is not easy to manufacture. The safety door of the present disclosure uses a manner that the inner side of the pressure-resistant shell is provided with a built-in groove, and the built-in groove is provided with a sealing gasket and a pressure-resistant built-in door, so as to avoid the risk of bursting or sinking. The disclosure of the high/low-pressure control valve makes the conversion of the high-pressure fluid and the low-pressure fluid controlled by one valve, which is simple and safe, greatly reduces the cost, and is the guarantee for the implementation of high/low-pressure household electric appliance.

The high/low pressure forming apparatus, 2 the safety door and 3 the high/low-pressure control valve can be used in the refrigerator or the washing machine or a clothes processing machine the dish-washing machine or the pickling machine or the footwear foot-care machine, and can also be used in other wider fields.

BRIEF DESCRIPTION OF DRAWINGS

The solution and advantages of present disclosure will be described in detail with reference to the drawings. A high/low-pressure forming apparatus in the drawings includes a movement apparatus, a pressure forming rod, a pressure forming body, a pressure forming shell and a valve, and the valve includes a pressure suction valve and a pressurization valve. An arrow represents a direction of gas flow, the pressure suction valve and the pressurization valve is single-flow, and a safety valve is level-pressure dual-directional flow: a built-in groove and a built-in door of the safety door, and a valve shell and a valve body of a high/low-pressure control valve.

DETAILED DESCRIPTION

Hereinafter a preferred implementation mode of a household electric appliance with a high/low-pressure function of the present disclosure will be described in detail with reference to the accompanying drawings. In implementation mode 1, an intake check valve of a high/low-pressure forming apparatus is integrally formed with or coupled (via a pipe and a valve) with a compartment of an external device (such as a refrigerator, a variable-pressure washing machine, a clothes processing machine, a variable-pressure dish-washing machine, a pickling machine and a footgear foot-care machine) to generate a low pressure, and an exhaust check valve of a high/low-pressure forming apparatus is integrally formed with or coupled (via a pipe and a valve) with a compartment of an external device (such as a refrigerator, a washing machine, a dish-washing machine, a pickling machine, a floor scrubber and a clothes processing machine) to generate a high pressure. In implementation mode 2, a pressure-resistant shell is disposed on the household electric appliance, and a built-in groove, a sealing gasket and a pressure-resistant built-in door are disposed on the pressure-resistant shell. In implementation mode 3, it is illustrated the implementation mode of a high/low-pressure control valve with multiple flow channels.

Implementation Mode 1

Figure 1:
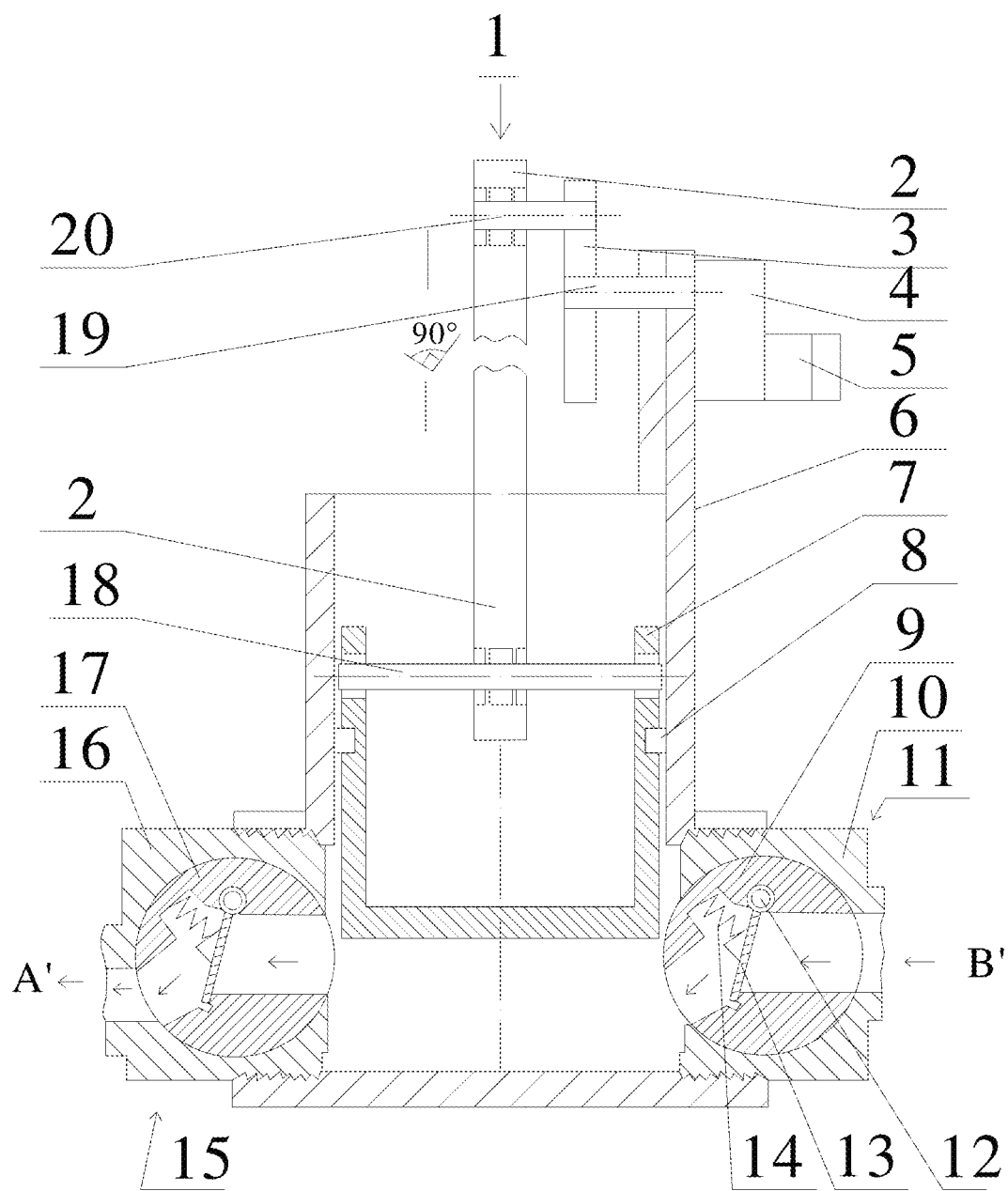
FIG. 1 is a schematic diagram of a high/low-pressure forming apparatus according to a first implementation mode of the present disclosure.
Figure 4:
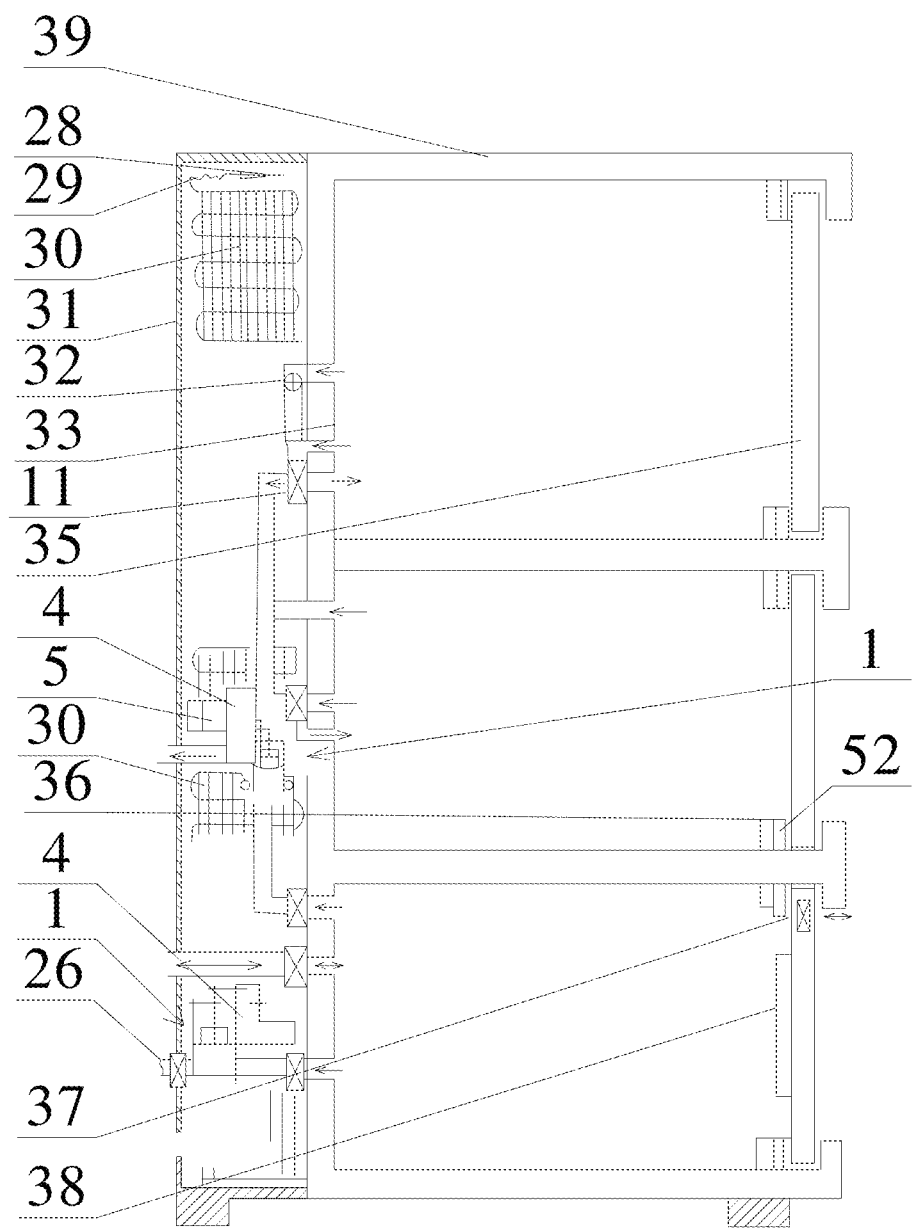
FIG. 4 is a schematic diagram of a refrigerator provided with a high/low-pressure forming apparatus, a safety door and a high/low-pressure control valve according to a fifth implementation mode of the present disclosure.
Figure 5:
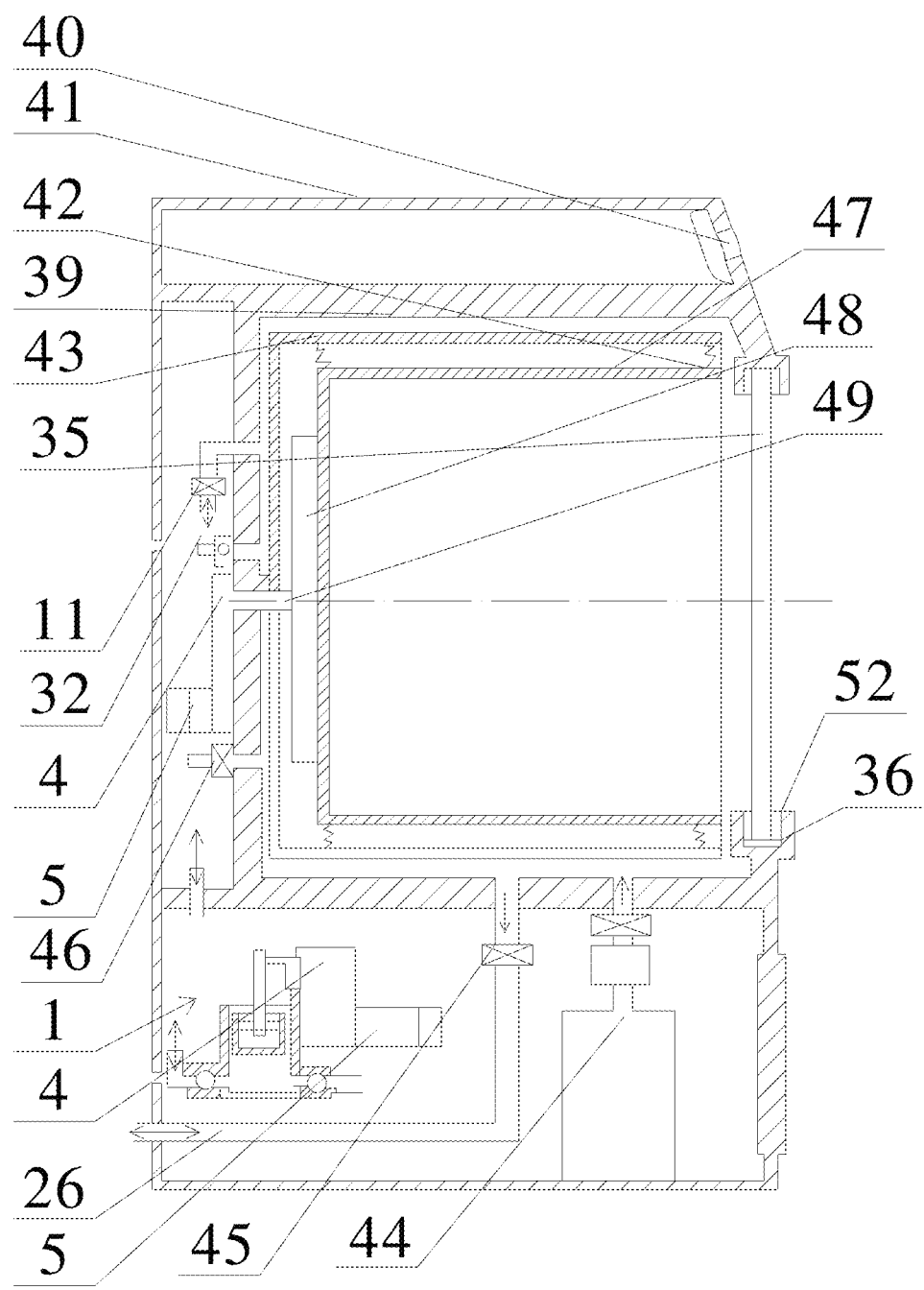
FIG. 5 is a schematic diagram of a washing machine provided with a high/low-pressure forming apparatus, a safety door and a high/low-pressure control valve according to a sixth implementation mode of the present disclosure.
Figure 6:
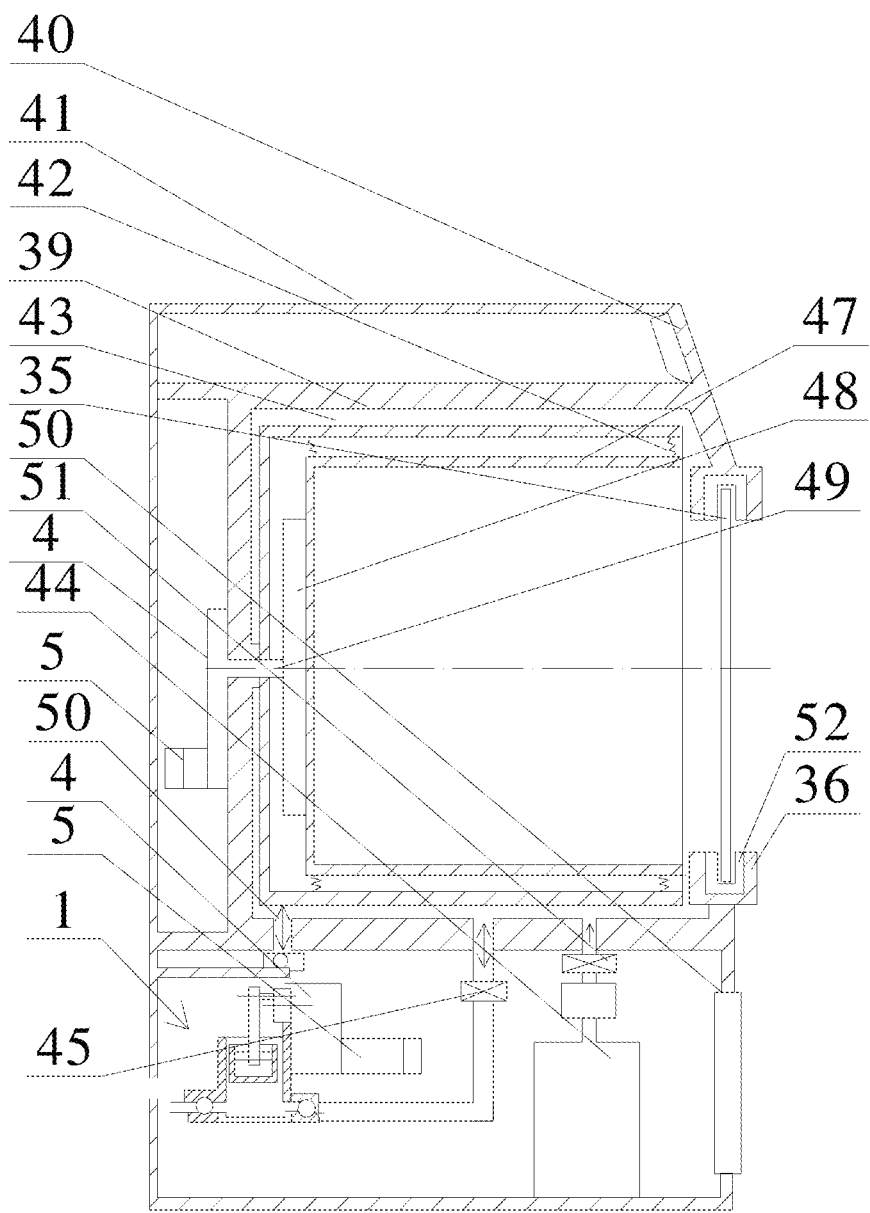
FIG. 6 is a schematic diagram of a clothes odor abatement machine provided with a high/low-pressure forming apparatus, a safety door and a high/low-pressure control valve according to a seventh implementation mode of the present disclosure.
Figure 7:
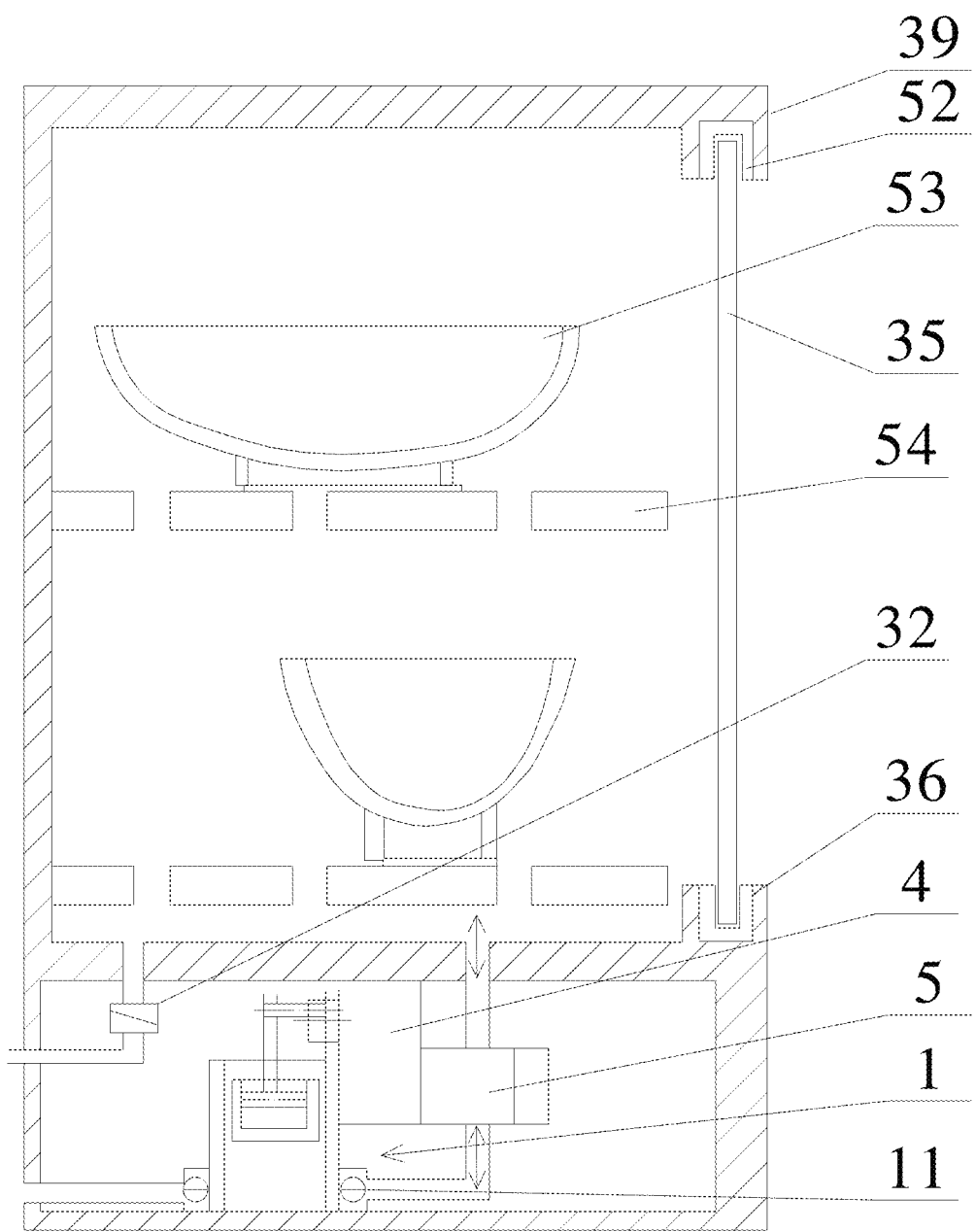
FIG. 7 is a schematic diagram of a dish-washing machine provided with a high/low-pressure forming apparatus, a safety door and a high/low-pressure control valve according to an eighth implementation mode of the present disclosure.
Figure 8:
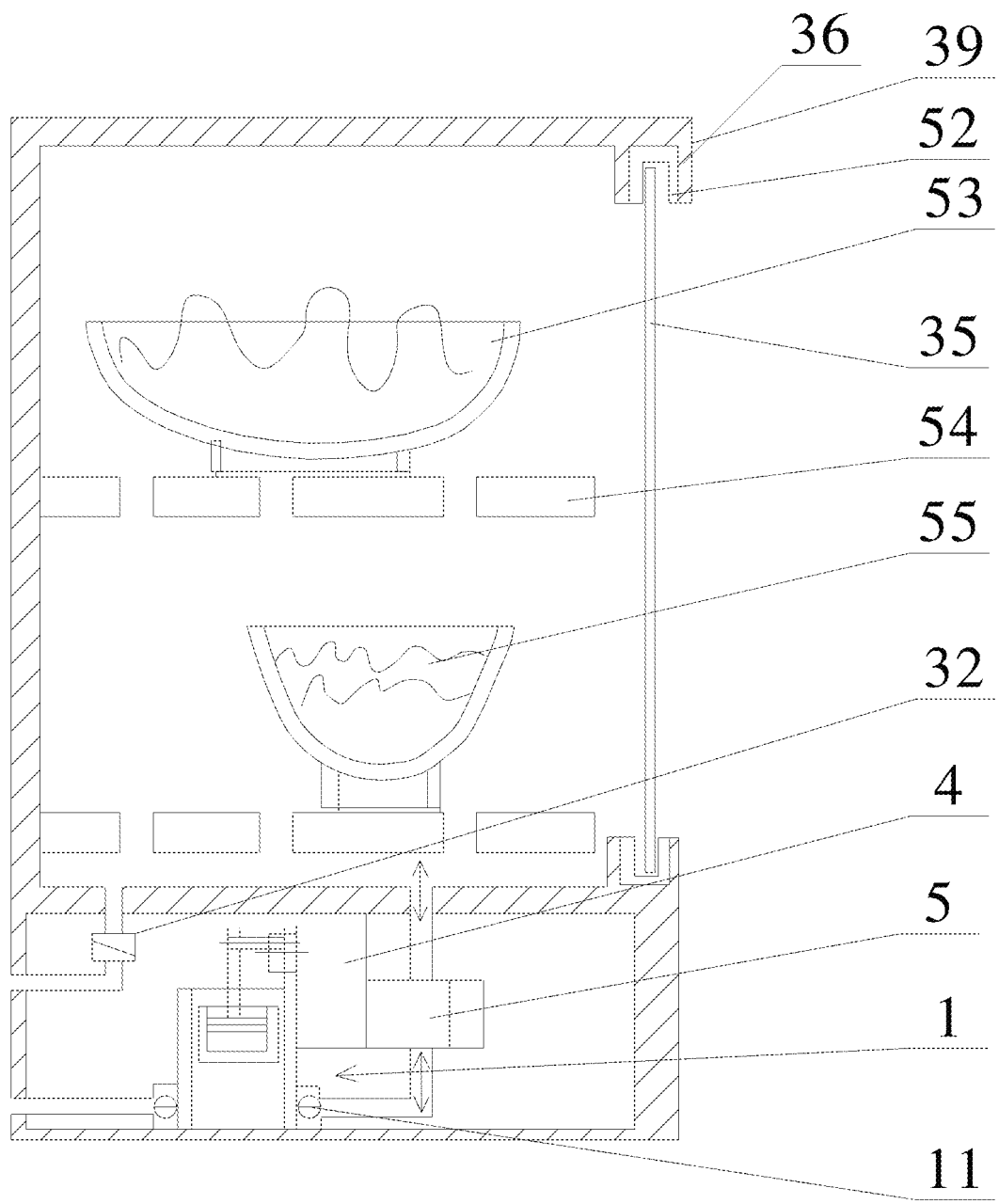
FIG. 8 is a schematic diagram of a pickling machine provided with a high/low-pressure forming apparatus, a safety door and a high/low-pressure control valve according to a ninth implementation mode of the present disclosure.
Figure 9:
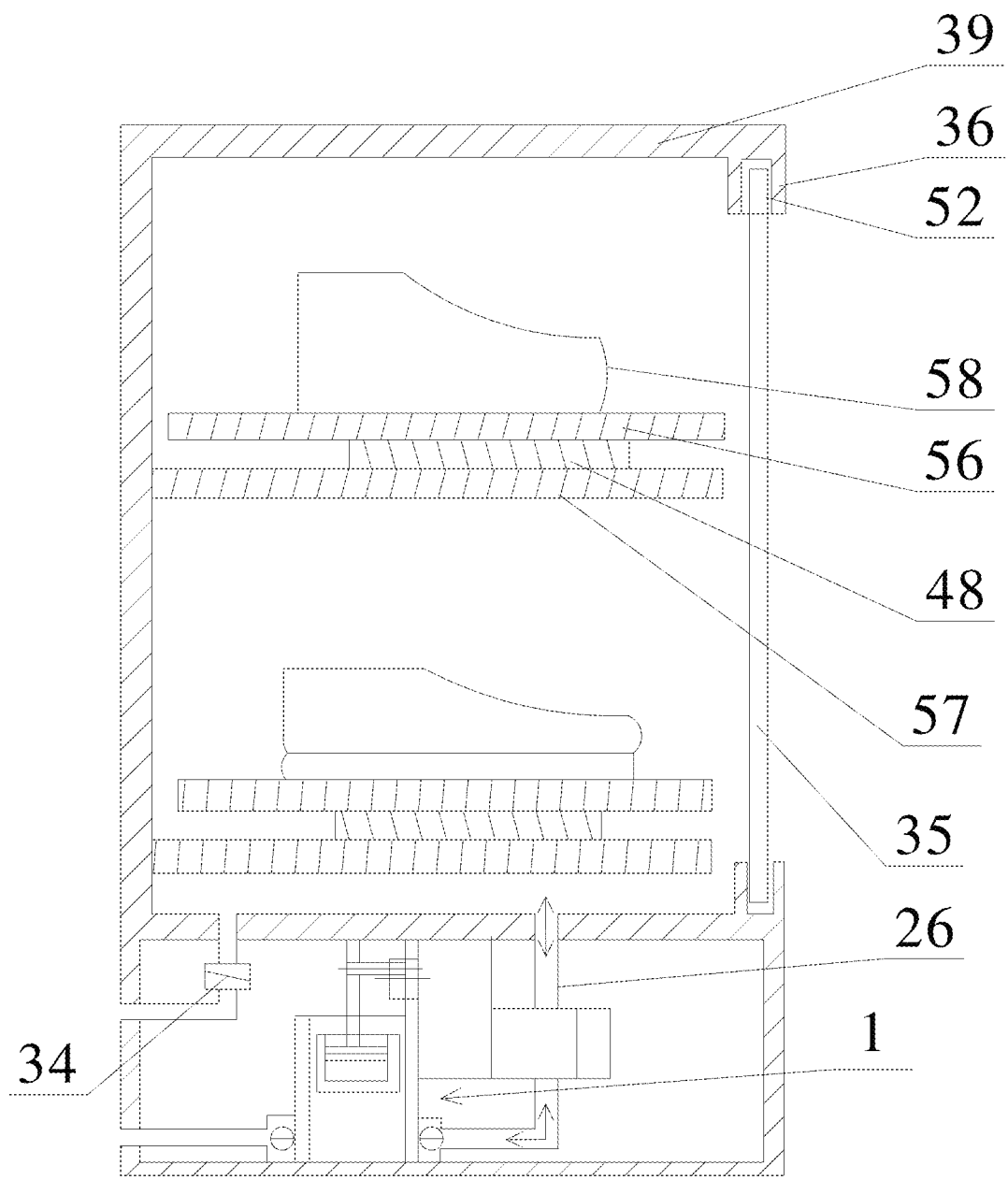
FIG. 9 is a schematic diagram of a footwear foot-care machine provided with a high/low-pressure forming apparatus, a safety door and a high/low-pressure control valve according to a tenth implementation mode of the present disclosure.
Figure 10:
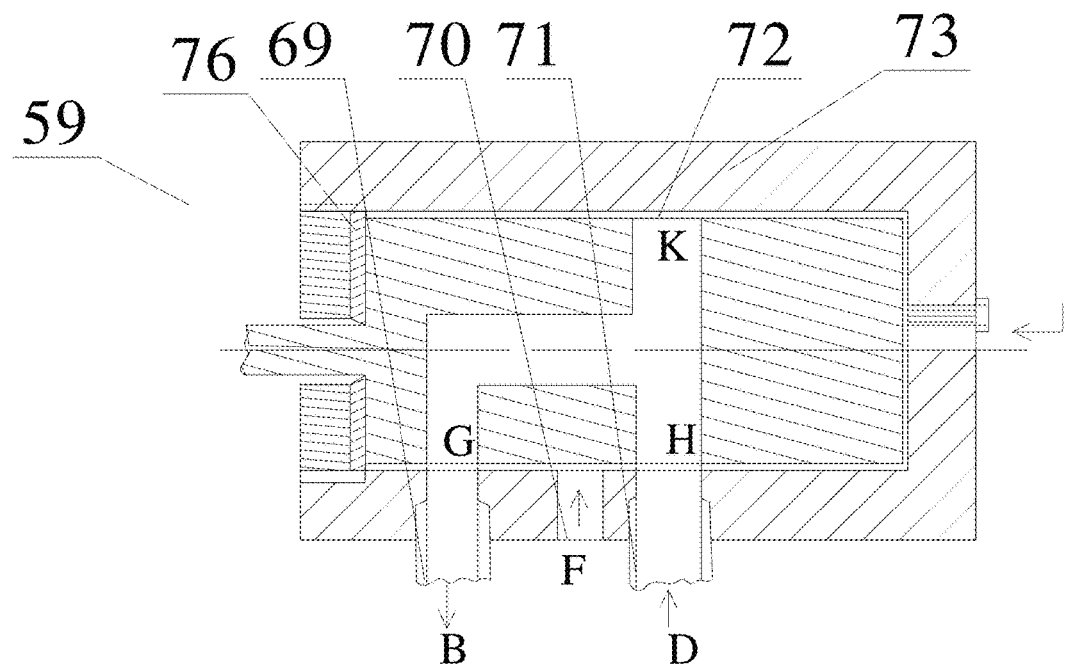
FIG. 10 is a schematic diagram of a high/low-pressure control valve according to a third implementation mode of the present disclosure.
Figure 11:
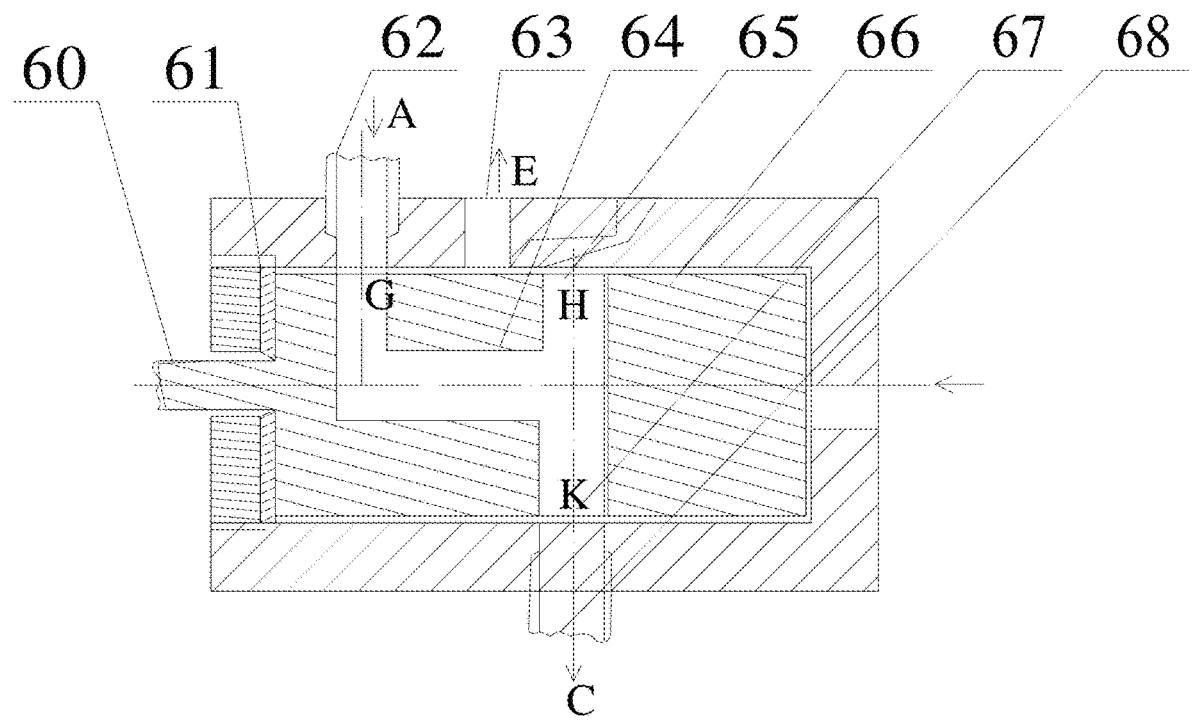
FIG. 11 is a schematic diagram of a high/low-pressure control valve according to the third implementation mode of the present disclosure.
Figure 12:
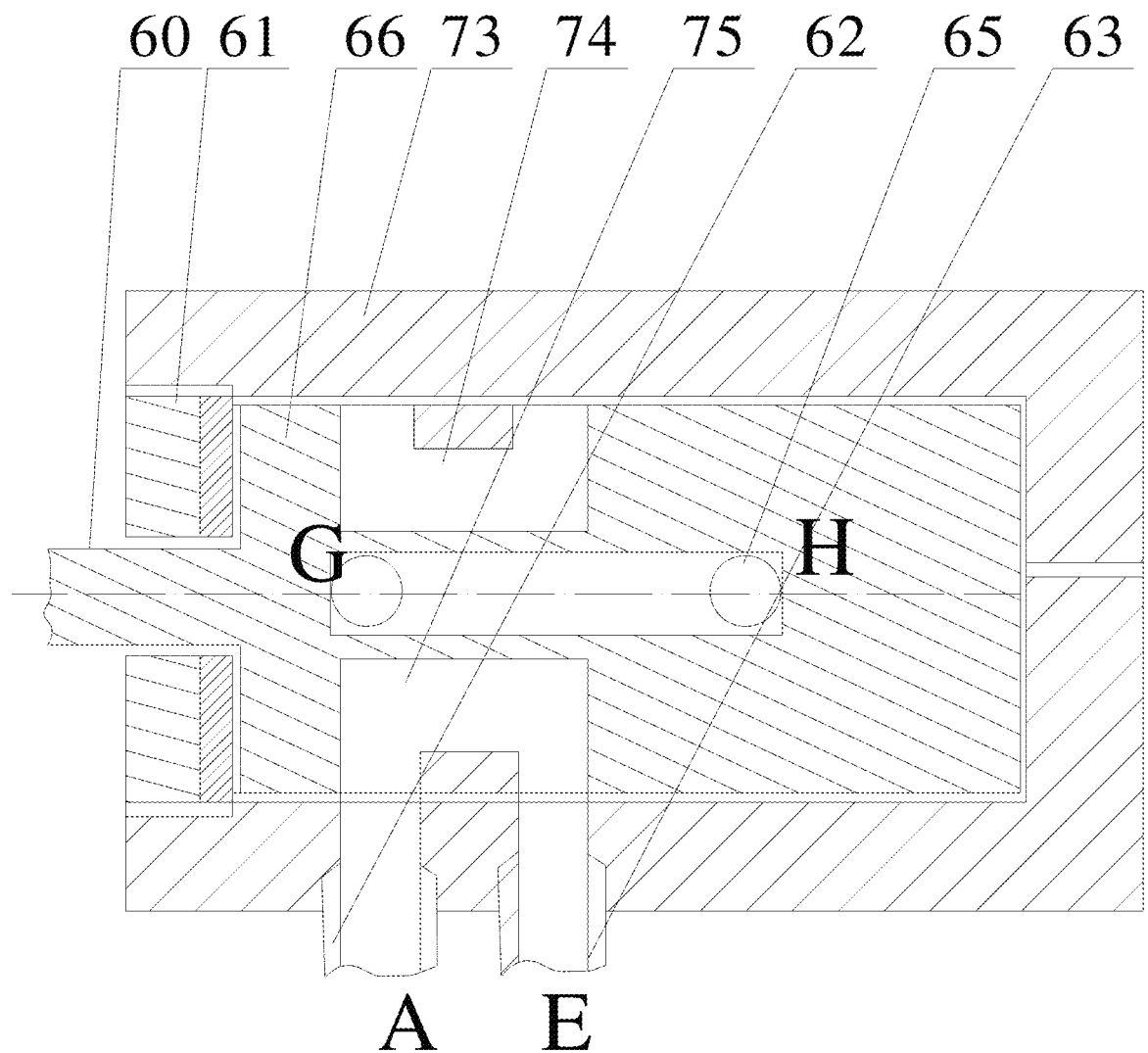
FIG. 12 is a schematic diagram of a high/low-pressure control valve according to the third implementation mode of the present disclosure.

As shown in FIGS. 1 and 4, a household electric appliance with a high/low-pressure function is provided in the implementation mode 1 of the present disclosure, and the household electric appliance with the high/low-pressure function includes a high-pressure compartment or a low-pressure compartment. The high-pressure compartment or the low-pressure compartment includes a pressure-resistant shell 39 and a safety door. A refrigerator prolongs the shelf life of food or drug by manufacturing a low-pressure environment in a cold storage chamber of a refrigeration device under a low-temperature condition to discharge odor of food or drug, hinder the survival of microbes with a low-oxygen environment and freeze food with a circle of a low pressure and a normal pressure. In the present disclosure, a high/low-pressure forming apparatus 1 is added to a refrigeration device such as the refrigerator, which is energy-saving, environmentally friendly and pollution-free. FIG. 4 shows a high/low-pressure forming device 1 provided with one pressure forming shell 6, and FIGS. 5 to 6 show a high/low-pressure forming device 1 provided with two pressure forming shells 6. Implementation mode 1 will be described with reference to FIGS. 1 and 4.

The refrigerator of the present disclosure includes a pressure-resistant shell 39, a built-in groove 36, a pressure-resistant sealing apparatus 80, a pressure regulating valve 37, a pressure-resistant built-in door 35, an inspection window 38, a dry filter 28, a capillary tube 29, a refrigeration system 30, a refrigerator shell 31, a safety valve 32 (restricting the maximum pressure and the minimum pressure), a refrigerator pressure-resistant inner-shell 33, a refrigerator resistant low-pressure upper door 35, a freezing chamber or a cold closet (i.e., a cold storage chamber) and a freezing refrigeration system 30.

The refrigerator of the present disclosure is provided with a high/low-pressure forming apparatus 1 including a movement apparatus 4, a pressure forming rod 2, a pressure forming body 7, a pressure forming shell 6 and a valve, where the valve includes a pressure suction valve and a pressurization valve, and the high/low-pressure forming apparatus 1 is a device for manufacturing a high-pressure space or a low-pressure space.

The cold storage chambers of various refrigeration devices such as the refrigerator achieve the purpose of food fresh keeping of food and odor removal through reducing the activity of microbes with low oxygen in a low pressure lower than the atmospheric pressure, low-pressure gas or fluid and low-temperature environment.

Various refrigeration devices such as refrigerators are each integrally provided with or coupled with the high/low-pressure forming apparatus 1, and an outer periphery of a bottom of the pressure forming shell 6 of the high/low-pressure forming apparatus 1 is integrally provided with or coupled with a pressurization valve 15 for manufacturing a pressure higher than an atmospheric pressure and a pressure suction valve 11 for manufacturing a pressure lower than the atmospheric pressure.

An air outlet (A') is disposed on the pressurization valve 15, and an air inlet (B') is disposed on the pressure suction valve 11.

The pressure suction valve integrally disposed on or coupled on the high/low-pressure forming apparatus 1 expels the gas in the cold storage chamber to form a low-pressure cold storage chamber in which the pressure is lower than the external atmospheric pressure.

The pressure forming shell 6 is integrally disposed on or coupled on the high/low-pressure forming apparatus 1, where an inner side of the pressure forming shell 6 is provided with one pressure forming body 7 which reciprocates axially along a hole wall in the pressure forming shell 6, the pressure forming body 7 is integrally provided with or coupled with one pressure forming rod 2 in a movable fit manner via a pressure forming body axis 18, and the other end of the pressure forming rod 2 is integrally provided with or coupled with the transmission apparatus 4 in the movable fit manner.

The pressure forming body 7 axially reciprocates along the hole wall in the pressure forming shell 6, and when the pressure forming body reciprocates to a position where space between the pressure forming body 7 in the pressure forming shell 6 and a bottom cover of the pressure forming shell 6 reaches the maximum and contains maximum amount of gas, the pressure forming body 7 compresses space of internal gas to form a high pressure, or when the pressure forming body 7 reciprocates to a position where space between the pressure forming body 7 in the pressure forming shell 6 and a bottom cover of the pressure forming shell 6 reaches the minimum and contains minimum amount of gas, the pressure forming body 7 expands space of internal gas to form a low pressure. A sealing ring 8 is disposed on the pressure forming body 7.

A cavity 10 of the pressure suction valve 11 is integrally provided with or coupled with a pressure suction valve rotating body 9 in a movable fit manner, a check valve 13 is integrally disposed in or coupled in the pressure suction valve rotating body 9, the pressure suction valve rotating body 9 is integrally disposed in or coupled in the cavity 10 of the pressure suction valve 11 in the movable fit manner. A cavity 16 of the pressurization valve is integrally provided with or coupled with a pressurization valve rotating body 17 in a movable fit manner, a check valve 13 is disposed in the pressurization valve rotating body 17, and a valve shaft 12 is disposed on the check valve 13. A spring 14 is disposed between the check valve 13 and the pressure suction valve rotating body 9, and a spring 14 is disposed between the check valve and the pressurization valve rotating body 17. The pressurization valve rotating body 17 is integrally disposed in or coupled in the cavity 16 of the pressurization valve in the movable fit manner.

A top end of each of the pressure suction valve rotating body and the pressurization valve rotating body is integrally provided with or coupled with a rotating handle, and the rotating handle is integrally provided with or coupled with a rotating apparatus.

A retaining spring is disposed on the check valve 13 disposed in the pressurization valve rotating body 17.

The high/low-pressure forming apparatus 1 achieves the mutual conversion of the high-pressure forming function and the low-pressure forming function of the high/low-pressure forming apparatus 1 through the rotation reverse of the valve rotating body.

A rotating apparatus 22 disposed on the pressure suction valve rotating handle 23 of the high/low-pressure forming apparatus 1 and a rotating apparatus 21 disposed on the pressurization valve rotating handle 25 of the high/low pressure forming apparatus 1 are integrally provided or coupled via the transmission apparatus 24.

The transmission apparatus 24 includes a gear drive, a pulley drive with a belt, a sprocket drive with a chain, a gear drive, or a shaft drive. The embodiment of the present disclosure takes a pulley and a transmission belt as an example.

The movement apparatus is integrally disposed on or coupled on the high/low-pressure forming apparatus 1, where the movement apparatus is driven by a motor 5 or an engine to drive a speed change mechanism or the pulley or a sprocket to rotate an eccentric gear 3, the eccentric gear 3 is integrally provided with or coupled with the pressure forming rod 2 in a movable fit manner through a connection rod axis 20, and the pressure forming body 7 and the pressure forming rod 2 are integrally provided or coupled in the movable fit manner to reciprocate along the pressure forming shell 6.

The high/low-pressure forming apparatus 1 involves a gear pump, a vane pump or a plunger pump, or the pressurization valve 15 and the pressure suction valve 11 involve the check valve, a plunger valve, a butterfly valve or a gate valve.

The valve is the check valve, the pressure suction valve 11 is a directional intake check valve, and the pressurization valve 15 is a directional exhaust check valve, or the check valve is rotated by a rotating body in the valve cavity to change the direction of fluid flow, and also known as a dual-direction check valve.

The outer periphery of the bottom of the pressure forming shell 6 of the high/low-pressure forming apparatus 1 is integrally provided with or coupled with the pressure suction valve 11 and the pressurization valve 15, the rotating apparatus of the pressure suction valve 11 and the rotating apparatus of the pressurization valve 15 are integrally provided or coupled via the transmission apparatus 4, the rotating handles are driven by the rotating apparatuses of the pressure suction valve and the pressurization valve to rotate and drive rotation reverse of the pressure suction valve rotating body and the pressurization valve rotating body so as to change a movement direction of an airflow in or out of the pressure forming shell 6 of the high/low-pressure forming apparatus 1, thereby switching a flow direction of a suctioning or outputting gas or fluid for the high pressure or the low pressure in a working compression chamber coupled with the high/low-pressure apparatus.

Figure 2:
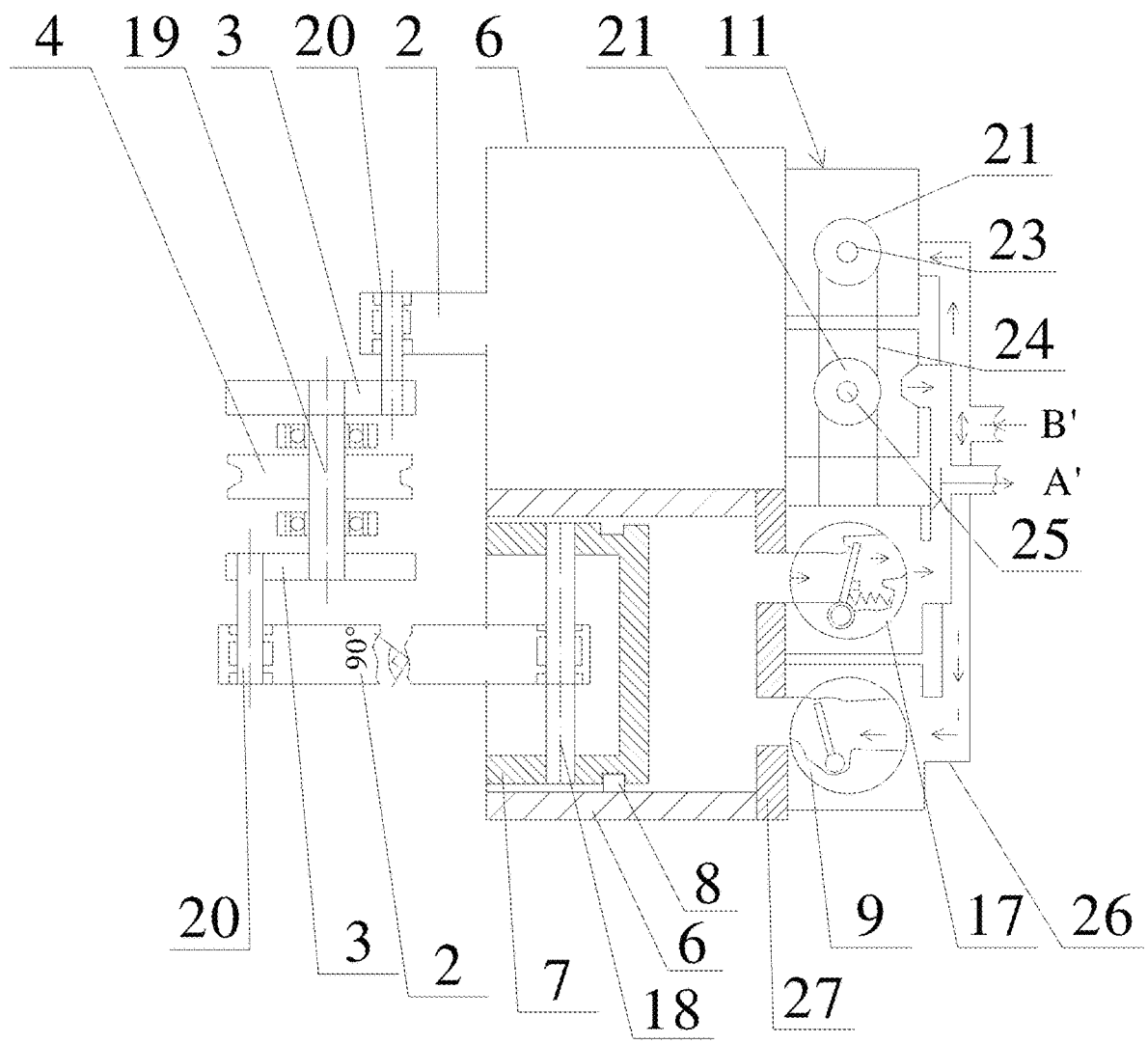
FIG. 2 is a schematic diagram of a high/low-pressure forming apparatus according to the first implementation mode and a fourth implementation mode of the present disclosure.
Figure 3:
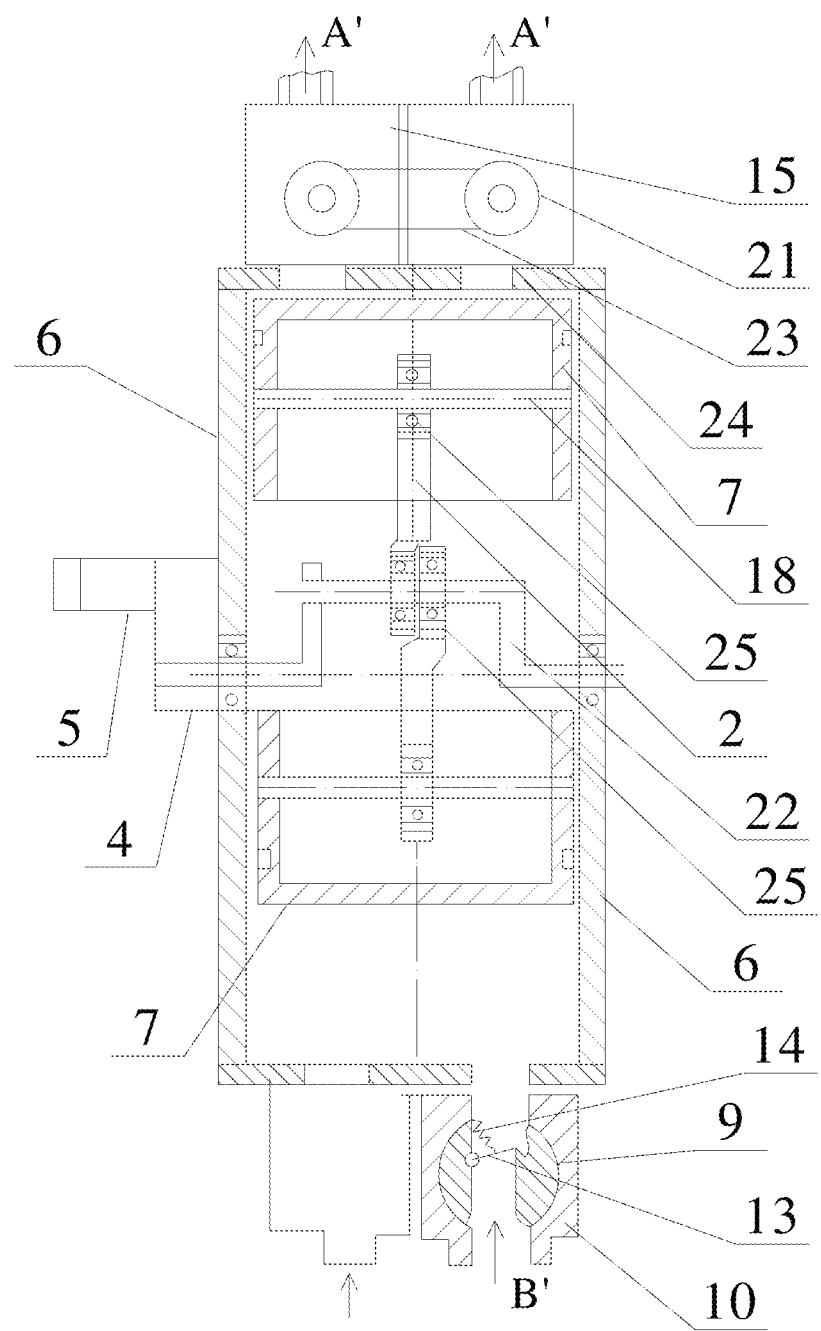
FIG. 3 is a schematic diagram of a high/low-pressure forming apparatus according to the first implementation mode and the fourth implementation mode of the present disclosure.

The high/low-pressure forming apparatus 1 shown in FIGS. 2 to 3 includes multiple pressure forming shells 6, and may continuously manufacture high-pressure gas or continuously expel gas.

Multiple pressure forming shells 6 are disposed on the high/low-pressure forming apparatus 1, one pressure forming body 7 which reciprocates axially along a hole wall in the pressure forming shell 6 is integrally disposed in or coupled in each of the multiple pressure forming shells 6, one pressure forming rod 2 is disposed on each pressure forming body 7 in a movable fit manner via the pressure forming body axis 18, each pressure forming rod 2 is integrally provided with or coupled with one eccentric gear 3 in a movable fit manner or each eccentric gear 3 is integrally provided with or coupled with two pressure forming rods 2 in a movable fit manner; and at least two eccentric gears 3 are integrally provided or coupled with the transmission apparatus 4 via a transmission axis 19; or the outer periphery of the bottom of each pressure forming shell 6 is integrally provided with or coupled with at least one pressurization valve 15 and at least one pressure suction valve 11. The pressurization valves 15 or the pressure suction valves 11 of the pressure forming shells 6 of the high/low-pressure forming apparatus 1 are integrally provided with or coupled with compartments, i.e., the high-pressure compartments or the low-pressure compartments, of multiple external devices via high/low-pressure control valves 59 and pipes 26.

The outer periphery of the bottom of each pressure forming shell 6 is integrally provided with or coupled with at least one pressure suction valve 11. The pressure suction valves 11 of the pressure forming shells 6 of the high/low-pressure forming apparatus 1 are integrally provided with or coupled with compartments of the multiple external devices via high/low-pressure control valves 59 and pipes 26 to form and manufacture multiple externally coupled low-pressure spaces; or the outer periphery of the bottom of each pressure forming shell 6 is integrally provided with or coupled with at least one pressurization valve 15. The pressurization valves 15 of the pressure forming shells 6 of the high/low-pressure forming apparatus 1 are integrally provided with or coupled with compartments of the multiple external devices via high/low-pressure control valves 59 and pipes 26 to form and manufacture multiple outer coupled high-pressure spaces.

When the pressure forming body 7 reciprocates in the pressure forming shell 6 to reach the top end of the pressure forming shell 6 which is far away from the bottom end of the pressure forming shell 6, the space in the pressure forming shell 6 is enlarged, and the space occupied by the gas in the pressure forming shell 6 is enlarged to form a low pressure; or when the pressure forming body 7 reciprocates in the pressure forming shell 6 to get close to the bottom end of the pressure forming shell 6, the space in the pressure forming shell 6 is reduced, and the gas in the pressure forming shell 6 is extremely compressed to form a high pressure.

The directional movement of airflow is formed in such a manner that the space in the pressure forming shell 6 is enlarged to form the low pressure or the space is reduced to form the high pressure.

The pressure suction valve 11 at an intake end is coupled with the external atmospheric environment, and the pressurization valve 15 at an exhaust end is integrally provided with or coupled with the working compression chamber to form a high/low-pressure forming apparatus 1 with the high pressure; or the pressurization valve 15 at an exhaust end is coupled with the external atmospheric environment, and the pressure suction valve 11 at an intake end is integrally provided with or coupled with the working compression chamber to form a high/low-pressure forming apparatus 1 with the low pressure; or a three-way reversing valve (not shown) is disposed on the pipe, and the three-way reversing valve is cooperated with the pressure suction valve 11 and the pressurization valve 15 to regulate the airflow direction.

The movement apparatus includes a power system, and the power system includes a motor or an engine.

The high/low-pressure forming apparatus 1 includes the movement apparatus, a pressure forming rod 2, a pressure forming body 7, a pressure forming shell 6 and a valve, where the valve includes a pressure suction valve 11 and a pressurization valve 15. The conversion of the high pressure and the low pressure of the working compression chamber coupled with the high/low-pressure forming apparatus 1 is achieved by changing a direction of the pressure suction valve 11 or a direction of the pressurization valve 15, in which one of the pressure suction valve 11 and the pressurization valve 15 is coupled with the refrigerator and the other of the pressure suction valve 11 and the pressurization valve 15 is coupled with the external atmospheric space.

The high/low-pressure forming apparatus 1 shown in FIG. 3 includes two pressure forming shells 6 which are integrally provided or coupled, and can continuously manufacture high-pressure gas or continuously expel gas.

The two pressure forming shells 6 are integrally provided or coupled. Two pressure forming bodies 7 are oppositely disposed in a direction of axially reciprocating along an inner bore of the two pressure forming shells 6, and one pressure forming rod 2 is integrally disposed on or coupled on each pressure forming body 7 in a movable fit manner via the pressure forming body axis 18. The two pressure forming rods 6 are integrally provided with or coupled with one eccentric shaft 22 in a movable fit manner.

The power apparatus drives the eccentric shaft 22 to rotate via the transmission apparatus, and the eccentric shaft 22 drives the pressure forming bodies 7 to reciprocate along an opposite direction in the pressure forming shell 6 via the two pressure forming rods 2.

An outer periphery of a bottom of the pressure forming shell 6 is integrally provided with or coupled with one or more pressure suction valves 11 and one or more pressurization valves 15.

The high/low-pressure apparatus 1 includes a movement apparatus, a pressure forming rod 2, a pressure forming body 7, a pressure forming shell 6, and a valve. The valve includes a pressure suction valve 11 and a pressurization valve 15. With such configuration, a high efficiency, high-speed and high/low-pressure forming apparatus for rapidly pumping and discharging gas or pressurizing gas is formed. The high/low-pressure forming apparatus 1 has a simple structure, light weight, low power consumption, high efficiency, and large pressure difference between the high pressure and the low pressure, can effectively manufacture the low pressure or the high pressure in the compartment, and thus has widely application. Dirty gas, germs and molds are pumped into the atmosphere by utilizing the pressure reduction effect, which is beneficial to fresh keeping of food. Thus, the troublesome problem of cleaning the cold storage chamber of the refrigerator is solved, and the problem of processing the clothes is solved. Pickling food under the high-pressure is quick, which can effectively reduce toxic and harmful chemical components slowly produced in the pickling process, and effectively prevent a threat to people's health caused by food deterioration. Many household electric appliances, various experimental devices or other devices requiring the high-pressure environment or the low-pressure environment are developed by using the effects of the low-pressure recovery or pumping and discharging, and the high-pressure penetration or dissolution.

Implementation Mode 2

As shown in FIGS. 4 to 9 and 13 to 14, a household electric appliance with a high/low-pressure function according to the implementation mode 2 of the present disclosure is provided with a safety door. The household electric appliance of the present disclosure uses a manner of manufacturing a low-pressure environment or a high-pressure environment, and achieves functions of low-pressure sterilization, decontamination, high-pressure penetration and the like by adding a high/low-pressure forming apparatus 1, which is energy-saving, environmentally friendly and pollution-free. In a high/low-pressure state, a shell of the household electric appliance is subjected to the action of the atmospheric pressure, and a closed door cannot adapt this situation and is dangerous, therefore, the household electric appliance is provided with a pressure-resistant shell 39. A built-in groove 36 is disposed on the pressure-resistant 39, a pressure-resistant built-in door 35 moves in the built-in groove 36 to achieve a function of opening or closing, thus avoiding hidden dangers of outward collapsing of the electric appliance door under the high-pressure and inward collapsing of the electric appliance door under the low-pressure.

Figure 13:
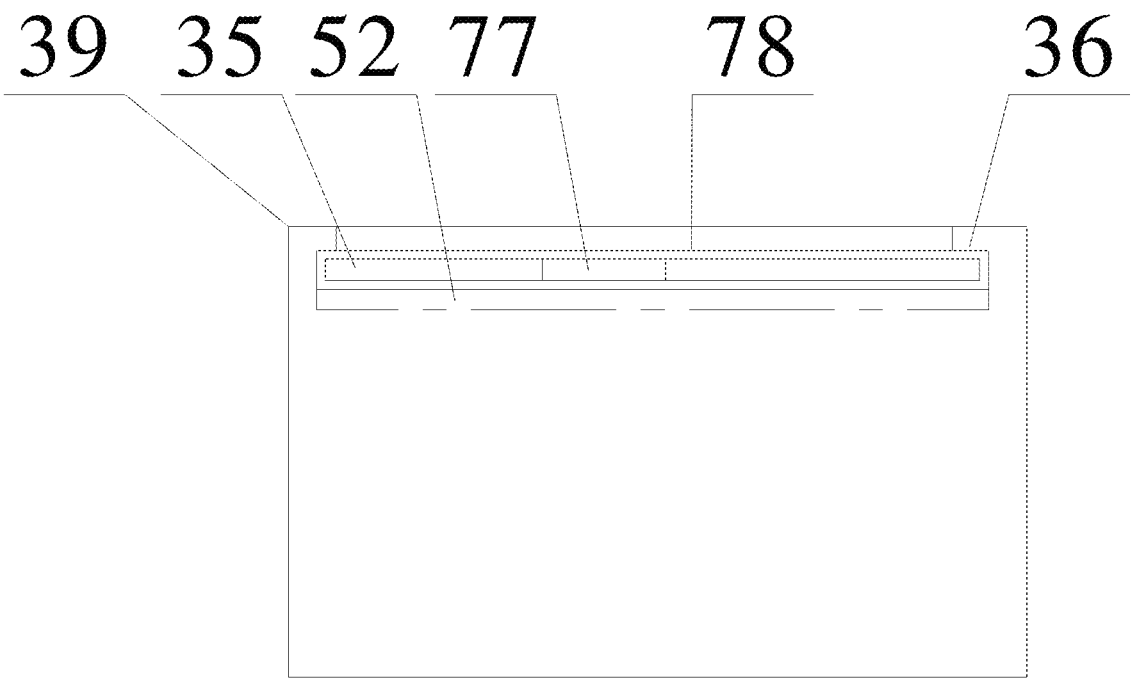
FIG. 13 is a schematic diagram of a pressure-resistant built-in door and a built-in groove disposed on a pressure-resistant shell according to a second implementation mode of the present disclosure.
Figure 14:
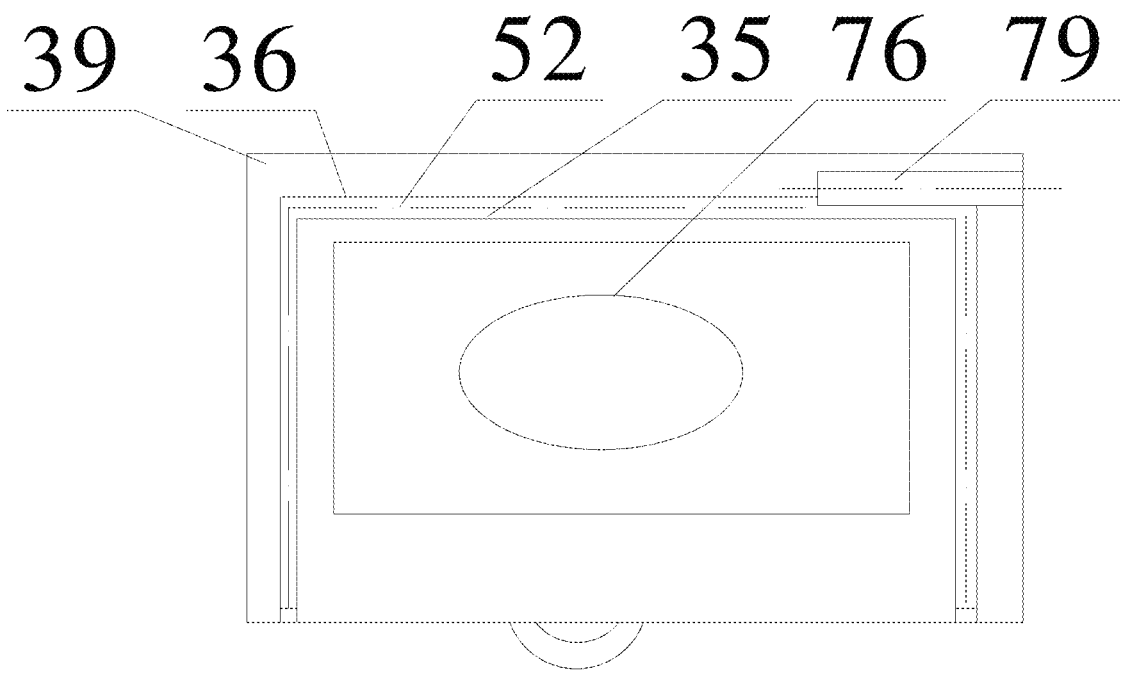
FIG. 14 is a schematic diagram of a pressure-resistant built-in door and a built-in groove disposed on a pressure-resistant shell according to a second implementation mode of the present disclosure.

FIGS. 4 to 9 illustrate a refrigerator, a variable-pressure washing machine, a deodorizing and perfuming machine, a variable-pressure dish-washing machine, a pickling machine and a footgear foot-care machine provided with the safety door, respectively. Pressure-resistant safety doors are disposed on pressure-resistant shells 39 of the household electric appliances. FIG. 13 is a side view of a pressure-resistant safety door, and FIG. 14 is a front view of a pressure-resistant safety door.

The household electric appliance with the high/low-pressure function includes a high/low-pressure forming apparatus 1. The high/low-pressure forming apparatus 1 includes a movement apparatus, a pressure forming rod 2, a pressure forming body 7, a pressure forming shell 6 and a valve, where the valve includes a pressure suction valve 11 and a pressurization valve 15, and the high/low-pressure forming apparatus 1 is a device for manufacturing a high-pressure compartment or a low-pressure compartment.

The pressure-resistant shell 39 is disposed on the household electric appliance with the high/low-pressure function, and an inner side of the pressure-resistant shell 39 is controlled by the high-pressure gas generated by the pressurization valve 15 of the high/low-pressure forming apparatus 1 via the valve to form a high-pressure compartment of the household electric appliance with the high/low-pressure function; or an inner side of the pressure-resistant shell 39 is controlled by the low-pressure gas generated by the pressure suction valve 11 of the high/low-pressure forming apparatus 1 via the valve to form a low-pressure compartment of the household electric appliance with the high/low-pressure function.

An inner side of the pressure-resistant shell 39 is integrally provided with or coupled with a built-in groove 36, and a pressure-resistant sealing apparatus 80 (i.e., a sealing gasket) and a pressure-resistant built-in door 35 is disposed in the built-in groove 36.

An outer end of one side of the built-in groove 36 is integrally provided with an opening on the pressure-resistant shell 39. The pressure-resistant built-in door 35 is disposed in the built-in groove 36 via the pressure-resistant sealing apparatus 80. The pressure-resistant built-in door 35 is completely pushed into a sealing state in the built-in groove 36 via a groove-shaped opening, and the high-pressure gas generated by the pressurization valve 15 of the high/low-pressure forming apparatus 1 is controlled by the valve to form a high-pressure compartment inside the pressure-resistant shell 39 of the household electric appliance with the high/low-pressure function; or the low-pressure gas generated by the pressure suction valve 11 of the high/low-pressure forming apparatus 1 is controlled by the valve to form a low-pressure compartment inside the pressure-resistant shell 39 of the household electric appliance with the high/low-pressure function.

After the pressure-resistant built-in door 35 is pulled in the built-in groove 36 via the groove-shaped opening to allow the pressure of the built-in groove 36 to be balanced with the pressure of the external atmosphere environment, the pressure-resistant built-in door 35 continues to move outwardly along the groove-shaped opening in the built-in groove 36 to an open state, and then articles in the pressure-resistant shell 39, i.e., the high-pressure compartment or the low-pressure compartment, can be taken out.

The pressure-resistant shell is disposed on the household electric appliance with the high/low-pressure function.

The low-pressure compartment or the high-pressure compartment of the household electric appliance with the high/low-pressure function includes one pressure-resistant shell 39.

The low-pressure compartment or the high-pressure compartment of the household electric appliance with the high/low-pressure function includes multiple pressure-resistant shells 39.

One or more built-in grooves 36 are integrally disposed on or coupled on the pressure-resistant shell.

One or more pressure-resistant sealing apparatuses 80 are disposed in each built-in groove 36 in the pressure-resistant shell.

One or more pressure-resistant sealing apparatuses 80 and one or more pressure-resistant built-in doors 35 are disposed in each built-in groove 36 in the pressure-resistant shell.

One or more transparency inspection windows 76 are disposed on each pressure-resistant built-in door 35 in the pressure-resistant shell.

One or more groove-shaped openings 78 are disposed on the pressure-resistant shell.

A handle 77 or a notch-shaped handle 77 is disposed on the pressure-resistant shell.

One or more pressure-resistant built-in doors 35 are disposed in a door frame of each groove-shaped opening of the pressure-resistant shell.

One or more pressure-regulating grooves 79 are disposed on each built-in groove of the pressure-resistant shell.

An inspection window is disposed on the pressure-resistant built-in door 35, a pressure-regulating groove (not shown) is disposed on the built-in groove 36, and an exit of the pressure-regulating groove is disposed at the bottom of the household electric appliance with the high/low-pressure function.

Implementation Mode 3

As shown in FIGS. 1 to 3 and 10 to 12, a high/low-pressure control valve 59 of a household electric appliance with a high/low-pressure function is provided in the implementation mode 3 of the present disclosure. On the basis of the implementation mode 1 and the implementation mode 2, a pressure forming device of the present disclosure adds a high/low-pressure control valve 59. Since the household electric appliance of the present disclosure uses the high/low-pressure forming apparatus 1 to manufacture a low-pressure environment or a high-pressure environment or perform a conversion between a low-pressure environment and a high-pressure environment, a traditional valve used to control the high/low-pressure is very complicated, difficult to control, and easy to cause accidents. The present disclosure merely needs a power apparatus to control the forward and reverse rotation of a valve handle 60 of the high/low-pressure control valve 59 to manufacture a high-pressure environment or a low-pressure environment. The high/low-pressure control valve 59 is integrally disposed on or coupled on the high/low-pressure forming apparatus 1, and the high/low-pressure control valve 59 includes a valve shell 73, a valve body 66 and a valve deck 61.

A pressurization port 62 (A), a pressure reduction port 68 (B), an air evacuation port 71 (D), an air filling port 68 (C), a circulating air inlet 63 (E) and a circulating air outlet 70 (F) are disposed on the valve shell 73. A three-way hole 64, a circulating air intake hole 74, a circulating air vent hole 75 and a sealing gasket 76 are disposed on the valve body 66.

An upper part of the valve body 66 is integrally provided with or coupled with a valve handle 60, and the valve handle 60 is coupled with a transmission apparatus and driven by the transmission apparatus to rotate. The three-way hole 64 is disposed on the valve body 66, and the three-way hole 64 cooperates with the pressurization port 62 (A), the pressure reduction port 69 (B), the air evacuation port 71 (D) and the air filling port 68 (C), and the vent port 69 (C) to form a closing or opening movable fit. The circulating air intake hole 74 is disposed on the valve body 66, and the circulating air intake hole 74 cooperates with the pressurizing port 62 (A), the pressure reduction port 68 (B), the air evacuation port 71 (D) and an air filling port 68 (C) via the circulating air inlet 63 (E) and the circulating air outlet 70 (F) to form a closing or opening fit for a high pressure or a low pressure.

At least one or more three-way holes 64 are disposed on the valve body of the high/low-pressure control valve.

At least one or more circulating air intake holes 74 and at least one or more circulating air vent holes 75 are disposed on the valve body of the high/low-pressure control valve.

At least one or more pressurization ports, at least one or more circulation ports and at least one or more circulating air outlets are disposed on the valve shell of the high/low-pressure control valve.

At least one or more pressure reduction ports, at least one or more circulation ports and at least one or more circulating air inlets are disposed on the valve shell of the high/low-pressure control valve.

A sealing cover is disposed at the bottom of the valve shell of the high/low-pressure control valve.

The bottom of the valve shell of the high/low-pressure control valve is provided with a lubrication hole, and the lubrication hole is sealed by a screw.

The pressurization port 62 (A) of the high/low-pressure control valve 59 and the air outlet (A') of the high/low-pressure forming apparatus 1 are integrally provided or coupled. An inner port of the pressurization port 62 (A) is coupled with an inner port of the air filling port 68 (C) via an G port disposed on the valve body 66 and an K port of the three-way hole 64, an outer port of the air filling port 68 (C) is coupled with the pressurization port of the household electric appliance with the high/low-pressure function. The pressure reduction port 69 (B) of the high/low-pressure control valve 59 and the air inlet (B') of the high/low-pressure forming apparatus 1 are integrally provided with or coupled with. The inner port of the pressure reduction port 69 (B) is coupled with an inner end of the circulating air inlet (F) 70 via the circulating air intake hole 74, and the gas is sucked into the circulating air inlet (F) 70. The pressure reduction port 69 (B) of the high/low-pressure control valve 59 and the air inlet (B') of the high/low-pressure forming apparatus 1 are integrally provided or coupled. The air evacuation port 71 (D) of the high/low-pressure control valve 59 is coupled with the pressure reduction port of the household electric appliance with the high/low-pressure function, at the same time, an inner port of the air evacuation port 71 (D) is not coupled with an H port of the three-way hole 64 and in a sealing state. The high-pressure gas of the high/low-pressure forming apparatus 1 enters into the pressurization port 62 (A) of the high/low-pressure control valve 59 through the air outlet (A') disposed on the pressurization valve 15, and the high-pressure environment in the pressure-resistant shell 39 of the household electric appliance is formed via the K port of the three-way hole 64 coupled with the inner port of the air inlet 68 (C) and the outer port of the air inlet 68 (C) coupled with the pressurization port of the household electric appliance with the high/low-pressure function. The air evacuation port 71 (D) of the pressure reduction port of the household electric appliance and the three-way hole 64 are in a sealing state.

The transmission apparatus drives the valve handle 60 of the high/low-pressure control valve 59 to rotate so that the G port disposed on the three-way hole 64 of the valve body 66 is coupled with the inner port of the pressure reduction port 69 (B) of the high/low-pressure control valve 59, the H port of the three-way hole 64 is coupled with the inner port of the air evacuation port 71 (D), and the inner port of the pressurizing port 62 (A) is coupled with the inner end of the F port of the high/low-pressure control valve 59 via the circulating air vent hole 75 disposed on the valve body 66. The inner port of the pressurization port 62 (A) is coupled with the inner port of the circulating air outlet 63 (E) via the circulating air vent hole 75, and the gas is discharged from the circulating air outlet 63 (E). An inner of the air filling port 68 (C) of the high/low-pressure control valve 59 is not coupled with the K port of the three-way hole 64 and in a sealing state. The outer port of the air evacuation port 71 (D) is coupled with the pressure reduction port of the household electric appliance with the high/low-pressure function to pump the gas out of the household electric appliance so as to form a low-pressure environment in the pressure-resistant shell 39. The air filling port 68 (C) of the pressurizing port of the household electric appliance and the three-way hole 64 are in a sealing state.

As described above, by changing a coupling mode of the high/low-pressure control valve 59, positions of the circulating air intake hole 74 and the circulating air vent hole 75 are lowered to heights matched with the air evacuation port 71 (D), the air filling port 68 (C), the circulating air inlet 63 (E) and the circulating air outlet 70 (F) respectively, for example, the air evacuation port 71 (D) of the high/low-pressure control valve 59 and the vent port (A') of the high/low-pressure forming apparatus 1 are integrally provided with or coupled with, or the air filling port 68 (C) of the high/low-pressure control valve 59 and the inlet port (B') of the high/low-pressure forming apparatus 1 are integrally or coupled and formed to be integrally disposed together, and the inner port of the pressure reduction port 69 (B) is coupled with the circulating air outlet 70 (F) via the circulating air intake hole 74. As described above, a state control of the high-pressure environment or the low-pressure environment of the household electric appliance is also achieved.

The high/low-pressure control valve 59 described above is a double channel conversion control valve.

According to the above structure, since the household electric appliance is provided with the high/low-pressure forming apparatus 1 to manufacture a high-pressure environment or a low-pressure environment, regardless of picking and placing articles, it is necessary to regulate the balance between a pressure in the storage chamber of the household electric appliance and the atmospheric pressure, therefore, continuous regulation is required. The traditional valve is complicated to regulate, and it is difficult to safely achieve the pressure regulation. The implementation mode of the present disclosure can effectively and quickly achieve the cycle conversion of high pressure, low pressure or normal pressure, and ensure the effect of high/low-pressure household electric appliance.

Implementation Mode 4

As shown in FIGS. 1 to 4 and 10 to 12, a fourth implementation mode of the present disclosure provides a high/low-pressure forming apparatus 1 based on the first implementation mode to the third implementation mode. The present disclosure adopts a manner of freezing and processing food with high-pressure and low-pressure circulation environment by manufacturing a high-pressure environment or a low-pressure environment under the low-temperature condition in a cold storage chamber or a cold closet of a refrigeration apparatus such as a refrigerator. According to the present disclosure, the high/low-pressure forming apparatus 1 is added to the refrigeration device, where FIG. 4 shows a high/low-pressure forming apparatus 1 provided with one pressure forming shell 6, and FIG. 2 shows a high/low-pressure forming apparatus 1 provided with two pressure forming shells 6. Implementation mode 4 will be described with reference to FIG. 1.

In this implementation mode, the high/low-pressure forming apparatus 1, a high/low-pressure control valve 59 and a pressure-resistant built-in door 35 are disposed in the refrigerator.

The refrigerator of the present disclosure includes a pressure-resistant shell 39, a built-in groove 36, a pressure-resistant sealing apparatus 80, a pressure regulating valve 37, a pressure-resistant built-in door 35, an inspection window 38, a dry filter 28, a capillary tube 29, a refrigeration system 30, a refrigerator shell 31, a safety valve 32 (restricting the maximum pressure and the minimum pressure), a refrigerator pressure-resistant inner-shell 33, a refrigerator resistant low-pressure upper door 9, a freezing chamber or a cold closet (i.e., a cold storage chamber), a freezing refrigeration system 30, a refrigerator resistant high-pressure lower door 1, a refrigerator pressure-resistant door and a high/low-pressure forming apparatus 1. The high/low-pressure forming apparatus 1 includes a movement apparatus, a pressure forming rod 2, a pressure forming body 7, a pressure forming shell 6 and a valve. The valve includes a pressure suction valve 11 and a pressurization valve 15. The high/low-pressure forming apparatus 1 is a device for manufacturing a high-pressure compartment or a low-pressure compartment.

A scheme in which two pressure-resistant shells 6 of the second implementation mode are integrally provided or coupled and are disposed side-by-side is as below.

The cold storage chambers of various refrigeration devices such as a refrigerator perform processing, pickling and fresh keeping of food in a manner of high-pressure infiltration or low-pressure decomposition in a high-pressure higher than the atmospheric pressure and low-temperature environment or in a low-pressure lower than the atmospheric pressure and low-temperature environment.

Various refrigeration devices such as the refrigerator are each integrally provided with or coupled with the high/low-pressure forming apparatus 1. The high/low-pressure forming apparatus 1 is integrally provided with or coupled with a pressurization valve 15 for manufacturing a pressure higher than an atmospheric pressure and a pressure suction valve for manufacturing a pressure lower than the atmospheric pressure.

The pressurization valve 15 integrally disposed on or coupled on the high/low-pressure forming apparatus 1 increases the gas in the cold storage chamber to form a high-pressure cold storage chamber in which the pressure is higher than the external atmospheric pressure.

A high-pressure anti-opening safety door is disposed on the refrigerator, the safety door is provided with a manual safety valve 32, and a high-pressure locking apparatus 21 is disposed on the safety door of the refrigerator.

The high-pressure locking apparatus is locked by a locating pin ejected by an inside high pressure and is unlocked when the locating pin is repositioned in a normal pressure.

Two side-by-side pressure forming shells 6 are disposed on the high/low-pressure forming apparatus 1, one pressure forming body 7 which reciprocates axially along a hole wall in the pressure forming shell 6 is integrally disposed in or coupled in each of the multiple pressure forming shells 6, one pressure forming rod 2 is disposed on each pressure forming body 7 in a movable fit manner via the pressure forming body axis 18, the other end of each pressure forming rod 2 is integrally provided with or coupled with one eccentric gear 3 in a movable fit manner, and at least two eccentric gears 3 are integrally provided or coupled with the transmission apparatus 4.

The pressure forming body 7 axially reciprocates along the hole wall in the pressure forming shell 6, and when the pressure forming body reciprocates to a position where space between the pressure forming body 7 in the pressure forming shell 6 and a bottom cover of the pressure forming shell 6 reaches the maximum and contains maximum amount of gas, the pressure forming body 7 compresses space of internal gas to form a high pressure, or when the pressure forming body 7 reciprocates to a position where space between the pressure forming body 7 in the pressure forming shell 6 and a bottom cover of the pressure forming shell 6 reaches the minimum and contains minimum amount of gas, the pressure forming body 7 expands space of internal gas to form a low pressure.

An outer periphery of the bottom of each pressure forming shell 6 of the high/low-pressure forming apparatus 1 is integrally provided with or coupled with a pressurization valve 15 for manufacturing a pressure higher than an atmospheric pressure and a pressure suction valve 11 for manufacturing a pressure lower than the atmospheric pressure.

The pressure suction valve 11 and the pressurization valve 15 disposed on the pressure forming shell 6 of the high/low-pressure forming apparatus 1 are coupled with an external of the pressure forming shell 6; or a cold storage chamber with the low-pressure is disposed on the refrigerator and is manufactured in combination with a high-pressure cold storage chamber.

A scheme in which two pressure-resistant shells 6 of the second implementation mode are integrally provided or coupled and are oppositely disposed in a front and rear direction is as below.

Two pressure-resistant shells 6 are integrally disposed on or coupled on the high/low-pressure forming apparatus 1 and are oppositely disposed in a front and rear direction.

An inner side of each pressure forming shell 6 is provided with one pressure forming body 7 which reciprocates axially along a hole wall in the each pressure forming shell 6. One pressure forming rod 2 is integrally disposed on or coupled on each pressure forming body 7 in a movable fit manner. The other ends of the two pressure forming rods 2 are integrally provided with or coupled with the transmission apparatus 4 in the movable fit manner.

The pressure forming body 7 axially reciprocates along the hole wall in the pressure forming shell 6, and when the pressure forming body reciprocates to a position where space between the pressure forming body 7 in the pressure forming shell 6 and a bottom cover of the pressure forming shell 6 reaches the maximum and contains maximum amount of gas, the pressure forming body 7 compresses space of internal gas to form a high pressure, or when the pressure forming body 7 reciprocates to a position where space between the pressure forming body 7 in the pressure forming shell 6 and a bottom cover of the pressure forming shell 6 reaches the minimum and contains minimum amount of gas, the pressure forming body 7 expands space of internal gas to form a low pressure. A sealing ring 8 is disposed on the pressure forming body 7.

An outer periphery of the bottom of each pressure forming shell 6 of the high/low-pressure forming apparatus 1 is integrally provided with or coupled with a pressurization valve 15 for manufacturing a pressure higher than an atmospheric pressure and a pressure suction valve 11 for manufacturing a pressure lower than the atmospheric pressure.

The valve is the check valve, the pressure suction valve 11 is a directional intake check valve, and the pressurization valve 15 is a directional exhaust check valve, or the check valve is rotated by a rotating body in a valve cavity to change the direction of fluid flow, and also known as a dual-direction check valve.

The outer periphery of the bottom of the pressure forming shell 6 of the high/low-pressure forming apparatus 1 is integrally provided with or coupled with the pressure suction valve 11 and the pressurization valve 15, the rotating apparatus of the pressure suction valve 11 and the rotating apparatus of the pressurization valve 15 are integrally provided or coupled via the transmission apparatus 4, the rotating apparatus of the pressure suction valve 11 and the rotating apparatus of the pressurization valve 15 are integrally provided or coupled via the transmission apparatus 4, the rotating handles are driven by the rotating apparatuses of the pressure suction valve and the pressurization valve to rotate and drive rotation reverse of the pressure suction valve rotating body and the pressurization valve rotating body so as to change a movement direction of an airflow in or out of the pressure forming shell 6 of the high/low-pressure forming apparatus 1, hereby switching a flow direction of a suctioning or outputting gas or fluid for the high pressure or the low pressure in a working compression chamber coupled with the high/low-pressure apparatus.

The pressurization valves 15 of the two pressure forming shells 6 are integrally provided with or coupled with the valve via a pipe 26.

The pressure suction valves 11 of the two pressure forming shells 6 are integrally provided with or coupled with the valve via the pipe 26.

Two or more pressure forming shells 6 may be integrally provided or coupled and may continuously manufacture the low pressure or the high pressure; or a three-way reversing valve (not shown) is disposed on the pipe, and the three-way reversing valve is cooperated with the pressure suction valve 11 and the pressurization valve 15 to regulate the airflow direction.

The refrigerator is provided with a safety valve 32, and the safety valve 32 safely regulates the high pressure and the low pressure of the cold storage chamber via the air evacuation port.

When the food is refrigerated or frozen, the pollution gas is first pumped out by the high/low-pressure forming apparatus 1 and discharged into the external atmosphere, after the valve of the high/low-pressure forming apparatus 1 is automatically closed, the cold storage chamber is in a low-pressure state or a vacuum state, the safety valve 32 levels the internal pressure with the external pressure, and the refrigerator completes a purification process.

When the food is quickly pickled, the food is prepared and placed in the cold storage chamber, the pollution gas in the cold storage chamber is pumped out by the high/low-pressure forming apparatus 1 and discharged into the external atmosphere, after the valve of the high/low-pressure forming apparatus 1 is automatically closed, the cold storage chamber is in a low-pressure state or a vacuum state, the safety valve 32 levels the internal pressure and the external pressure, and then the high/low-pressure forming apparatus 1 pressurizes the cold storage chamber. After the pressure is kept for a fixed time, the safety valve 32 levels the internal pressure and the external pressure, and the pickled food may be taken out. After quickly pickling or seasoning at a low-temperature, the food can be prevented from deteriorating, and nutrient loss can be avoided.

The solution of the refrigerator is that a high/low-pressure forming apparatus 1 and the safety valve 32 are added to the refrigeration system 30 to achieve a cycle changing environment of a low pressure and a high pressure in which the low pressure is manufactured for odor removal and fresh keeping and the high pressure is manufactured for flavoring and fresh keeping.

The refrigerator discharges or reduces the gas inside the refrigerator via an air evacuation port, a high/low-pressure forming apparatus 1, a pressure suction valve and a pipe. The refrigerator increases the gas pressure inside the refrigerator via the high/low-pressure forming apparatus 1, a pressurization valve and a pipe.

The refrigerator is provided with a safety valve 32, and the safety valve 32 safely regulates the high pressure and the low pressure in the cold storage chamber, a freezing chamber or a storage chamber via the air evacuation port.

Two high/low-pressure forming apparatuses 1 are disposed in combination or integrally, and are coupled via the pipe to continuously manufacture the high pressure or the low-pressure efficiently. The two high/low-pressure apparatuses 1 both include a movement apparatus, a pressure forming rod 2, a pressure forming body 7, a pressure forming shell 6, and a valve. The valve includes a pressure suction valve 11 and a pressurization valve 15. With such configuration, a high efficiency, high-speed, high/low-pressure forming apparatus for rapidly pumping and discharging gas or pressurizing gas is formed. The high/low-pressure forming apparatus 1 has a simple structure, light weight, low power consumption, high efficiency, large pressure difference between the high pressure and the low pressure, can effectively manufacture the compartment with the low pressure or the high pressure, and has widely application. Dirty gas and germs and molds are pumped into the atmosphere by utilizing the pressure reduction effect, which is beneficial to fresh keeping of food. Thus, the troublesome problem of cleaning the cold storage chamber of the refrigerator is solved, and the problem of processing the clothes is solved. Pickling food under the high pressure is quick, which can effectively reduce toxic and harmful chemical components slowly produced in the pickling process, and effectively prevent a threat to people's health caused by food deterioration. Many household electric appliances, various experimental devices or other devices requiring the high-pressure environment or the low-pressure environment are developed by using the effects of the low-pressure recovery or pumping and discharging, and the high-pressure penetration or dissolution.

Implementation Mode 5

As shown in FIGS. 2 to 3 and 4, in this implementation mode based on first implementation mode to the fourth implementation mode, an inner side of a pressure-resistant shell 39 of a refrigerator forms a high-pressure compartment or a low-pressure compartment through a high/low-pressure forming apparatus 1, a high/low-pressure control valve 59 and a pressure-resistant built-in door 35 disposed on the pressure-resistant shell 39 based on first implementation mode to the fourth implementation mode.

The present disclosure adopts a manner of freezing and processing food with high-pressure, normal pressure and low-pressure circulation environment in a cold storage chamber under a low-temperature condition. FIG. 4 shows a high/low-pressure forming apparatus 1 provided with one pressure forming shell 6, and FIGS. 2 and 3 show a high/low-pressure forming apparatus 1 provided with two pressure forming shells 6. The high/low-pressure forming apparatus with multiple pressure forming shells 6 disposed on a refrigeration device of implementation mode 3 will be described with reference to FIGS. 2 and 3.

The refrigerator of the present disclosure includes a pressure-resistant shell 39, a built-in groove 36, a pressure-resistant sealing apparatus 80, a pressure regulating valve 37, a pressure-resistant built-in door 35, an inspection window 38, a dry filter 28, a capillary tube 29, a refrigeration system 30, a refrigerator shell 31, a safety valve 32 (restricting the maximum pressure and the minimum pressure), a refrigerator pressure-resistant inner-shell 33, a refrigerator resistant low-pressure upper door 9, a freezing chamber or a cold closet (i.e., a cold storage chamber), a freezing refrigeration system 30, a refrigerator resistant high-pressure lower door 1, a refrigerator pressure-resistant door and a high/low-pressure forming apparatus 1. The high/low-pressure forming apparatus 1 includes a movement apparatus, a pressure forming rod 2, a pressure forming body 7, a pressure forming shell 6 and a valve. The valve includes a pressure suction valve 11 and a pressurization valve 15. The high/low-pressure forming apparatus 1 is a device for manufacturing a high-pressure compartment or a low-pressure compartment.

Multiple pressure forming shells 6 are integrally disposed on or coupled on the high/low-pressure forming apparatus 1, one pressure forming body 7 which reciprocates axially along a hole wall in the pressure forming shell 6 is integrally disposed in or coupled in each of the multiple pressure forming shells 6, one pressure forming rod 2 is disposed on each pressure forming body 7 in a movable fit manner via the pressure forming body axis 18, each pressure forming rod 2 is integrally provided with or coupled with one eccentric gear 3 in a movable fit manner or each eccentric gear 3 is integrally provided with or coupled with two pressure forming rods 2 in a movable fit manner; and at least two eccentric gears 3 are integrally provided or coupled with the transmission apparatus 4; or the outer periphery of the bottom of each pressure forming shell 6 is integrally provided with or coupled with at least one pressurization valve 15 and at least one pressure suction valve 11. The pressurization valves 15 and the pressure suction valves 11 of the pressure forming shells 6 of the high/low-pressure forming apparatus 1 are integrally provided with or coupled with compartments of multiple external devices via high/low-pressure control valves 59 and pipes 26.

The pressure forming shell 6 is integrally disposed on or coupled on the high/low-pressure forming apparatus 1, where an inner side of the pressure forming shell 6 is integrally provided with or coupled with a pressure forming body 7 which reciprocates axially along a hole wall in the pressure forming shell 6. A pressure forming rod 2 is integrally disposed on or coupled on the pressure forming body 7 in a movable fit manner. One eccentric gear 3 is integrally disposed on or coupled on the pressure forming rod 2 in a movable fit manner. The eccentric gear 3 is integrally provided or coupled and is cooperated with the transmission apparatus to drive the pressure forming rod 2 and the pressure forming body 7 to reciprocate axially along the inner hole wall of the pressure forming shell 6.

The outer periphery of the bottom of the pressure forming shell 6 is integrally provided with or coupled with a pressurization valve 15 for manufacturing a pressure higher than an atmospheric pressure and a pressure suction valve 11 for manufacturing the pressure lower than the atmospheric pressure.

The pressure forming body 7 in the inner side of the pressure forming shell 6 axially reciprocates along the hole wall, and the pressure forming body 7 compresses the inner space to form a high pressure when the amount of gas inside the pressure forming shell 6 reaches the maximum m; or the pressure forming body 7 in the inner side of the pressure forming shell 6 axially reciprocates along the hole wall, and the pressure forming body 7 expands the inner space to form a low pressure when the amount of gas inside the pressure forming shell 6 reaches the minimum.

The outer periphery of the bottom of the pressure forming shell 6 is integrally provided with or coupled with the pressure suction valve 11 or the pressurization valve 15, and the pressure suction valve 11 or the pressurization valve 15 is coupled with a compartment of the external device of the pressure forming shell 6 via a high/low-pressure control valve 59 and a pipe 26.

The high/low-pressure forming apparatus 1 is integrally provided with or coupled with the multiple pressure forming shells 6. The outer periphery of the bottom of each pressure forming shell 6 is integrally provided with or coupled with at least one pressurization valve 15 and at least one pressure suction valve 11. The at least one pressure suction valve 11 of the each pressure forming shell 6 of the high/low-pressure forming apparatus 1 is coupled with the compartments, i.e., the cold closet or the freezing chamber, of the external device via the high/low-pressure control valve 59 and the pipe 26 to form and manufacture multiple externally coupled low-pressure spaces or high-pressure spaces.

A vibration disk may be disposed in a mesh, a paliform, a basket, a tubular or a box shape, and will not be described here.

According to the above structure, the cold storage chamber is disposed in the refrigerator pressure-resistant shell 39 to ensure safety, and the mold and peculiar smell are removed by using a low-pressure environment or gas environment or fluid environment without manual scrubbing and sterilization, so that chemical pollution of the existing chemical washing products is avoided. Circular pressure change of high pressure and normal pressure, normal pressure and low pressure, or low pressure and high pressure enables the cold storage chamber to discharge mold and peculiar smell and effectively removes bacteria or other harmful components adhered to food. In addition, the high-pressure pickling can shorten the processing time, the nutrient loss is avoided, the high-pressure pickling is very convenient, the efficiency is improved and the harm of food deterioration to human health is thus prevented.

The pressure-resistant shell 39 of the refrigerator may be provided with a spice bottle or a drug bottle via the valve and the pipe and the cold storage chamber, the cold storage chamber of the refrigerator may also be provided with a temperature-control apparatus to achieve the effects of deodorization, sterilization and prolonged preservation of the refrigerator, and the refrigerator can also be provided with a microcomputer and a keyboard apparatus (not shown) to achieve intelligent processing for food.

Although the refrigerator is described above as an example, however, the refrigerator of the present disclosure can also embody the present disclosure in a manner of partial technical, and the food preservation manner of the low pressure or vacuum sterilization of the present disclosure can also have more structural manners. In the above-described structure, the structure of the implementation mode and other combinations can be adopted.

Implementation Mode 6

As shown in FIGS. 1 to 3, 5 and 10 to 12, based on first implementation mode to the fifth implementation mode, a variable-pressure washing machine washes clothes in a manner of intensively decomposing and separating dirt and oil dirt on the clothes in a circulation change environment between a low pressure lower than the atmospheric pressure and a normal pressure in the washing chamber. The variable-pressure washing machine has the characteristics of energy conservation and environment protection and no pollution. The variable-pressure washing machine of the present disclosure is provided with a high/low-pressure forming apparatus 1, where FIG. 1 shows a high/low-pressure forming apparatus 1 provided with one pressure forming shell 6, and FIGS. 2 to 3 respectively show a high/low-pressure forming apparatus provided with two side-by-side pressure forming shells 6 and a high/low-pressure forming apparatus provided with two pressure forming shells 6 disposed oppositely in a front and rear direction. The implementation mode 6 will be described below with reference to FIGS. 1 to 3, 5 and 10 to 12.

In this implementation mode, an inner side of a pressure-resistant shell 39 of the viable-pressure washing machine forms a high-pressure compartment or a low-pressure compartment through a high/low-pressure forming apparatus 1, a high/low-pressure control valve 59 and a pressure-resistant built-in door 35 disposed on the pressure-resistant shell 39.

The variable-pressure washing machine of the present disclosure includes a pressure-resistant shell 39, a built-in groove 36, a pressure-resistant sealing apparatus 80, a pressure regulating valve 37, a pressure-resistant built-in door 35, an inspection window 38, a variable-pressure washing tub 41, a vibration apparatus 48, and a washing chamber 47 disposed in the pressure-resistant shell 39, where a water inlet valve 32, a drain valve 45, a vent valve 33 and a safety valve 46 are disposed on the washing chamber 47. A high/low-pressure forming apparatus 1 is disposed on the variable-pressure washing machine shell 11 and includes a movement apparatus, a pressure forming rod 2, a pressure forming body 7, a pressure forming shell 6 and a valve. The valve includes a pressure suction valve 11 and a pressurization valve 15. The high/low-pressure forming apparatus 1 is a device for manufacturing a high-pressure space or a low-pressure space.

FIG. 4 shows a high/low-pressure forming apparatus 1 provided with one pressure forming shell 6, FIGS. 5 and 6 show a high/low-pressure forming apparatus 1 provided with two pressure forming shells 6. The implementation mode 6 will be described below with reference to FIGS. 4 to 6.

Under normal pressure, the variable-pressure washing machine immerses clothes into a volatile detergent 45 in the washing chamber 47, and vibrates the clothes and the scrubbing solution at a constant frequency through a vibration apparatus 48 disposed in the washing chamber 47 of the variable-pressure washing machine, and the fluid containing the scrubbing solution 45 impacts the clothes to avoid mutual friction between the clothes and mutual friction between the clothes and the washing machine. The detergent directly rinses away the dirt and the oil dirt, and after washing and vibration are completed, the fluid is discharged out of the washing chamber 47. The pressure suction valve disposed on the high/low-pressure forming apparatus is coupled with the washing chamber 47 through a high/low-pressure control valve 59 and a pipe, and the exhaust gas in the washing chamber 47 is discharged. After low-pressure purification processing is completed, the variable-pressure washing machine resumes normal-pressure washing.

In another example, the variable-pressure washing machine washes clothes in a manner of intensively decomposing and separating dirt and oil dirt on the clothes in a low-pressure environment whose pressure is lower than the atmospheric pressure in the washing chamber, and vibrating the clothes through the vibration apparatus 48 at a low pressure to initially separate the dirt and oil dirt. The pressure-resistant shell 39 is provided with a safety valve 46 to provide a high-pressure limit or a low-pressure limit.

In another example, the vibration apparatus 48 vibrates the clothes at a low-pressure to initially separate the dirt and the oil dirt. The variable-pressure washing machine immerses clothes into the water solubility detergent 45 in the washing chamber 47, and vibrates the clothes and the scrubbing solution through a vibration apparatus 48 disposed in the washing chamber 47 of the variable-pressure washing machine, and the scrubbing solution impacts the clothes to avoid mutual friction between the clothes and mutual friction between the clothes and the washing machine. The scrubbing solution directly rinses away the dirt and the oil dirt, and after vibration are completed, the fluid is discharged out of the washing chamber 47 and the scrubbing solution is discharged after washing. The high/low-pressure forming apparatus is integrally disposed on or coupled on the variable-pressure washing machine. The high/low-pressure forming apparatus may generate a low-pressure lower than the atmospheric pressure, and the pressure forming shell of the high/low-pressure forming apparatus is integrally provided with or coupled with a pressurization valve for manufacturing a pressure higher than the atmospheric pressure and a pressure suction valve for manufacturing a pressure lower than the atmospheric pressure.

In the variable-pressure washing machine, the washing chamber 47 is integrally provided with or coupled with a pressure suction valve via the high/low-pressure control valve 59 and the pipe, and the pressure suction valve expels the gas or the fluid in the washing chamber 47 to form a low-pressure washing chamber 47 whose pressure is lower than the external atmospheric pressure.

The washing chamber 47 of the variable-pressure washing machine is driven by a motor 5 via the transmission apparatus 4 and a power output shaft 49 to rotate; or the washing chamber 47 is disposed in a washing cage 43; or a three-way reversing valve (not shown) is disposed on the pipe, and the three-way reversing valve is cooperated with the pressure suction valve 11 and the pressurization valve 15 to regulate the airflow direction.

The pressure forming shell 6 is integrally disposed on or coupled on the high/low-pressure forming apparatus 1, where an inner side of the pressure forming shell 6 is provided with one pressure forming body 7 which reciprocates axially along a hole wall in the pressure forming shell 6, the pressure forming body 7 is integrally provided with or coupled with one pressure forming rod 2 in a movable fit manner through a pressure forming body axis 18, and the other end of the pressure forming rod 2 is integrally provided with or coupled with the transmission apparatus 4 in the movable fit manner.

The pressure forming body 7 axially reciprocates along the hole wall in the pressure forming shell 6, and when the pressure forming body reciprocates to a position where space between the pressure forming body 7 in the pressure forming shell 6 and a bottom cover of the pressure forming shell 6 reaches the maximum and contains maximum amount of gas, the pressure forming body 7 compresses space of internal gas to form a high pressure, or when the pressure forming body 7 reciprocates to a position where space between the pressure forming body 7 in the pressure forming shell 6 and a bottom cover of the pressure forming shell 6 reaches the minimum and contains minimum amount of gas, the pressure forming body 7 expands space of internal gas to form a low pressure. A sealing ring 8 is disposed on the pressure forming body 7.

An outer periphery of the bottom of the pressure forming shell 6 of the high/low-pressure forming apparatus 1 is integrally provided with or coupled with the pressurization valve 15 for manufacturing a pressure higher than an atmospheric pressure and a pressure suction valve 11 for manufacturing the pressure lower than the atmospheric pressure.

A cavity 10 of the pressure suction valve 11 is integrally provided with or coupled with a pressure suction valve rotating body 9 in a movable fit manner, and a check valve 13 is disposed in the pressure suction valve rotating body 9. The pressure suction valve rotating body 9 is integrally disposed in or coupled in the cavity 10 of the pressure suction valve 11 in the movable fit manner. A cavity 16 of the pressurization valve is integrally provided with or coupled with a pressurization valve rotating body 17 in a movable fit manner, the check valve 13 is disposed in the pressurization valve rotating body 17, and a valve shaft 12 is disposed on the check valve 13. A spring 14 is disposed between the check valve 13 and the pressure suction valve rotating body 9, and a spring 14 is disposed between the check valve and the pressurization valve rotating body 17. The pressurization valve rotating body 17 is integrally disposed in or coupled in the cavity 16 of the pressurization valve in the movable fit manner.

A top end of each of the pressure suction valve rotating body and the pressurization valve rotating body is integrally provided with or coupled with a rotating handle, and the rotating handle is integrally provided with or coupled with a rotating apparatus.

The high/low-pressure forming apparatus 1 achieves the mutual switching between the high-pressure forming function and the low-pressure forming function of the high/low-pressure forming apparatus 1 through the rotation reverse of the valve handle 60 of the high/low-pressure control valve 59.

The transmission apparatus 24 includes a gear drive, a pulley drive with a belt, a sprocket drive with a chain, a gear drive, or a shaft drive. The embodiment of the present disclosure takes a pulley and a transmission belt as an example.

The movement apparatus is integrally disposed on or coupled on the high/low-pressure forming apparatus 1, where the movement apparatus is driven by a motor 5 or an engine to drive a speed change mechanism or the pulley or a sprocket to rotate an eccentric gear 3, the eccentric gear 3 is integrally provided with or coupled with the pressure forming rod 2 in a movable fit manner through a connection rod axis 20, and the pressure forming body 7 and the pressure forming rod 2 are integrally provided or coupled in the movable fit manner to reciprocate along the pressure forming shell 6.

The outer periphery of the bottom of the pressure forming shell 6 is integrally provided with or coupled with at least one pressure suction valve 11. The at least one pressure suction valve 11 of the pressure forming shell 6 of the high/low-pressure forming apparatus 1 is integrally provided with or coupled with inner spaces of multiple washing machine tubs 43 via a high/low-pressure control valve 59 and a pipe 26 to form and manufacture multiple low-pressure spaces in the washing machine tubs 43

In an example, the outer periphery of the bottom of the pressure forming shell 6 is integrally provided with or coupled with at least one pressurization valve 15. The at least one pressurization valve 15 of the pressure forming shell 6 of the high/low-pressure forming apparatus 1 is integrally provided with or coupled with inner spaces of multiple washing machine tubs 43 via a high/low-pressure control valve 59 and a pipe 26 to form and manufacture multiple high-pressure spaces in the washing machine tubs 43.

When the pressure forming body 7 reciprocates in the pressure forming shell 6 to reach the top end of the pressure forming shell 6 which is far away from the bottom end of the pressure forming shell 6, the space in the pressure forming shell 6 is enlarged, and the space occupied by the gas in the pressure forming shell 6 is enlarged to form a low pressure; or when the pressure forming body 7 reciprocates in the pressure forming shell 6 to get close to the bottom end of the pressure forming shell 6, the space in the pressure forming shell 6 is reduced, and the gas in the pressure forming shell 6 is extremely compressed to form a high pressure.

The directional movement of airflow is formed in such a manner that the space in the pressure forming shell 6 is enlarged to form a low pressure or the space is reduced to form a high pressure.

The pressure suction valve 11 at an intake end is coupled with the external atmospheric environment, and the pressurization valve 15 at an exhaust end is integrally provided with or coupled with the working compression chamber to form a high/low-pressure forming apparatus 1 with the high pressure; or the pressurization valve 15 at an exhaust end is coupled with the external atmospheric environment, and the pressure suction valve 11 at an intake end is integrally provided with or coupled with the working compression chamber to form a high/low-pressure forming apparatus 1 with the low-pressure.

The movement apparatus includes a drive system and a power system, where the drive system includes a pulley drive, a gear drive or a shaft drive, and the power system includes a motor and an engine.

Since the high/low-pressure forming apparatus 1 includes the movement apparatus, a pressure forming rod 2, a pressure forming body 7, a pressure forming shell 6 and a valve, where the valve includes a pressure suction valve 11 and a pressurization valve 15, a high efficiency, high-speed, high/low-pressure forming apparatus for rapidly pumping and discharging gas or fluid or pressurizing gas or fluid is formed. The high/low-pressure forming apparatus 1 has a simple structure, light weight, low power consumption, high efficiency, large pressure difference between the high pressure and the low pressure, can effectively manufacture the compartment with the low pressure or the high pressure, and has widely application. Dirty gas or fluid and germs and molds are pumped into the atmosphere by utilizing the pressure reduction effect.

Implementation Mode 7

As shown in FIGS. 2 to 3 and 5, in this implementation mode based on first implementation mode to the sixth implementation mode, an inner side of a pressure-resistant shell 39 of a variable-pressure washing machine forms a high-pressure compartment or a low-pressure compartment through a high/low-pressure forming apparatus 1, a high/low-pressure control valve 59 and a pressure-resistant built-in door 35 disposed on the pressure-resistant shell 39. On the basic of the first implementation mode to second implementation mode, a variable-pressure washing machine of the present disclosure washes clothes in a manner of intensively decomposing and separating dirt and oil dirt on the clothes in a low-pressure environment whose pressure is lower than the atmospheric pressure in the washing chamber, and intensively dissolving the detergent and permeating the dirt and the oil dirt on the clothes in a high-pressure environment whose pressure is higher than the atmospheric pressure, that is, the variable-pressure washing machine washes the clothes at a circularly changed pressure of the low pressure, the normal pressure and the high pressure. The variable-pressure washing machine of the present disclosure is provided with a high/low-pressure forming apparatus 1, where FIG. 1 shows a high/low-pressure forming apparatus 1 provided with one pressure forming shell 6, and FIGS. 2 to 3 shows a high/low-pressure forming apparatus provided with two side-by-side pressure forming shells 6 and a high/low-pressure forming apparatus provided with two pressure forming shells 6 disposed oppositely in a front and rear direction. The implementation mode 7 will be described below in brief with reference to FIGS. 1 to 3 and 4 to 6 and implementation modes 1 to 6.

The variable-pressure washing machine of the present disclosure includes a variable-pressure washing machine shell 11, a pressure-resistant build-in door 35, a vibration apparatus 48 and a washing chamber 47, where a water inlet valve 32, a drain valve 45 and a breather valve are disposed on the washing chamber 47, and a high/low-pressure forming apparatus is disposed on the variable-pressure washing machine shell 11. The high/low-pressure forming apparatus includes a movement apparatus, a transmission apparatus, a pressure forming rod 2, a pressure forming body, a pressure forming shell and a valve, where the valve includes a pressure suction valve and a pressurization valve.

FIG. 4 shows a high/low-pressure forming apparatus 1 provided with one pressure forming shell 6, FIG. 3 shows a high/low-pressure forming apparatus 1 provided with two pressure forming shells 6 disposed together. The implementation mode 7 will be described below in brief with reference to FIGS. 1 to 2, 5 and 10 to 12 and implementation modes 1 to 6.

A scheme in which multiple pressure-resistant shells 6 of the third implementation mode are integrally provided or coupled is as below.

The variable-pressure washing machine washes clothes in a manner of intensively decomposing and separating dirt and oil dirt on the clothes in a low-pressure environment whose pressure is lower than the atmospheric pressure in the washing chamber 47, and intensively dissolving the detergent and permeating the dirt and the oil dirt on the clothes in a high-pressure environment whose pressure is higher than the atmospheric pressure in the washing chamber 47.

Multiple pressure forming shells 6 are disposed on the high/low-pressure forming apparatus 1, one pressure forming body 7 which reciprocates axially along a hole wall in the pressure forming shell 6 is integrally disposed in or coupled in each of the multiple pressure forming shells 6, two pressure forming rods 2 are disposed on each pressure forming body 7 in a movable fit manner via the pressure forming body axis 18. The outer periphery of the bottom of each pressure forming shell 6 is integrally provided with or coupled with at least one pressurization valve 15 and at least one pressure suction valve 11. The pressurization valves 15 or the pressure suction valves 11 of the pressure forming shells 6 of the high/low-pressure forming apparatus 1 are integrally provided with or coupled with compartments, i.e., the high-pressure compartments or the low-pressure compartments, of multiple external devices via high/low-pressure control valves 59 and pipes 26.

Two pressure forming shells 6 are integrally disposed on or coupled on the high/low-pressure forming apparatus 1, where inner sides of the two pressure forming shells 6 are respectively provided with two pressure forming bodies 7 which reciprocate axially along hole walls in the two pressure forming shells 6, each pressure forming body 7 is integrally provided with or coupled with one pressure forming rod 2 in a movable fit manner, and the two pressure forming rods 2 are integrally provided with or coupled with one eccentric shaft 22 in the movable fit manner. The eccentric shaft 22 is integrally provided with or coupled with a motor 5 via the movement apparatus 4.

The pressure forming body 7 in the inner side of the pressure forming shell 6 axially reciprocates along the hole wall, and when the internal gas or fluid space reaches the maximum, extreme compression is performed to form a high pressure, or when the internal gas or fluid space reaches the minimum, extreme expansion is performed to form a low pressure. The outer periphery of the bottom of the pressure forming shell 6 is integrally provided with or coupled with the pressure suction valve 11 or the pressurization valve 15, and the pressure suction valve 11 or the pressurization valve 15 is coupled with an inner space of the external device of the pressure forming shell 6 via the high/low-pressure control valve 59 and the pipe 26.

The pressure suction valve 11 and the pressurization valve 15 are respectively coupled with the inner space of the external device of the pressure forming shell 6 via the high/low-pressure control valve 59 and the pipe 26 to achieve a circularly changing of the low pressure, the normal pressure and the high pressure.

According to the above structure, since washing clothes in the low pressure or normal pressure or high-pressure environment reduces or saves water consumption, no or only a small amount of water as a carrier is needed, reducing waste of water resources, reducing the using amount of scrubbing solution and improving the efficiency.

In winter, the washed clothes can be dewatered and heated by a temperature-control apparatus via the pressure suction valve, and then the clothes can be taken out and worn.

From the above structure, it can be seen that the variable-pressure washing machine can at least adopt a pulsator washing machine tub or a roller washing machine tub. A spice bottle or a fiber repair liquid bottle can be disposed on the variable-pressure washing machine shell and communicated with the pressure-resistant shell 39 through the valve and the pipe. The pressure-resistant shell 39 of the variable-pressure washing machine can also be provided with the temperature-control apparatus to maintain a certain temperature of clothes after being washed in winter, and the variable-pressure washing machine can also be provided with a microcomputer and a keyboard apparatus 49 to achieve intelligent washing.

According to the above structure, the pressure-resistant shell 39 is disposed in the variable-pressure shell 40 to ensure safety, and the dirt is removed by using a high-pressure environment, low-pressure environment or vacuum environment without drastic knead effect, so that mechanical damage to clothes is reduced. The method of using scrubbing solution or washing gas to decompose and vaporize dirt avoids the chemical damage of the existing variable-pressure washing machine using chemical washing products to the clothes. Through a high pressure or low-pressure environment of at least one time and discharging gas or fluid of at least one time, not only can the dirt be discharged, but bacteria or other harmful components adhered to the clothes can also be effectively removed. Such washing method eliminates the need to dry the clothes, and after washing, the clothes can be taken out and worn, which is very convenient, prolongs the service period of the clothes, greatly reduces power consumption, and eliminates environmental pollution.

According to the above structure, since washing clothes in the high-pressure, low pressure or vacuum environment requires almost no water or very little water as a carrier, the waste of water resources is reduced, where carbon dioxide or special volatile detergent may be used as the washing gas, or industrial waste gas can be effectively utilized to improve the utilization rate of rubbish.

A high/low-pressure technology and a vibration technology of the variable-pressure washing machine can be configured on different washing machines so that the clothes can be washed only through the high-low change of the pressure or the washing function can be enhanced through the high-low change of the pressure, thereby reducing or eliminating environmental pollution.

Implementation Mode 8

A deodorizing and perfuming machine is shown in FIGS. 1 to 3, 6 and 10 to 12, and in this implementation mode based on the first implementation mode to the seventh implementation mode, an inner side of a pressure-resistant shell 39 of a deodorizing and perfuming machine forms a high-pressure compartment or a low-pressure compartment through a high/low-pressure forming apparatus 1, a high/low-pressure control valve 59 and a pressure-resistant built-in door 35 disposed on the pressure-resistant shell 39. A high/low-pressure forming apparatus 1 is disposed on the deodorizing and perfuming machine and includes a movement apparatus, a pressure forming rod 2, a pressure forming body 7, a pressure forming shell 6 and a valve. The valve includes a pressure suction valve 11 and a pressurization valve 15. The high/low-pressure forming apparatus 1 is a device for manufacturing a high-pressure space or a low-pressure space.

The deodorizing and perfuming machine cleans the clothes in the pressure-resistant shell 39 in a manner of strengthening the deodorant and permeating and dissolving dirt and oil dirt on the clothes in a high-pressure environment whose pressure is higher than the atmospheric pressure, adding spice or drug after the exhaust gas is discharged at a normal pressure, and then spraying the spice or drug into the clothes in a high-pressure state.

The deodorizing and perfuming machine is provided with the pressure-resistant shell 39, and a build-in groove 36, a pressure-resistant sealing apparatus 80 and a pressure-resistant build-in door 35 are disposed on the pressure-resistant shell 39. A pressurization valve 15 and a vent valve are disposed in the pressure-resistant shell 39 of the deodorizing and perfuming machine, a valet stand is disposed in the pressure-resistant shell 39, and the clothes is placed on the valet stand. In the pressure-resistant shell 39, after the deodorant is sprayed on the clothes, a high pressure is applied or a vibration apparatus 48 vibrates to discharge exhaust gas, and after the spice or drug is sprayed on the clothes, the high pressure is applied, the vibration apparatus 48 is disposed in the pressure-resistant shell 39 to generate vibration at a certain frequency. The vibration apparatus can vibrate the clothes inside the deodorizing and perfuming machine. The spice or drug is strongly penetrated into the clothes under the high pressure in the pressure-resistant shell 39, the vibration apparatus 48 vibrates to strengthen the penetration function, gas is discharged by the safety valve 46 after continuous high-pressure treatment to achieve a normal pressure, and then the clothes are taken out.

Implementation Mode 9

A variable-pressure dish-washing machine is shown in FIGS. 1 to 3, 7 and 10 to 12. Based on first implementation mode to the eighth implementation mode, an inner side of a pressure-resistant shell 39 of a variable-pressure dish-washing machine of the present disclosure forms a high-pressure compartment or a low-pressure compartment through a high/low-pressure forming apparatus 1, a high/low-pressure control valve 59 and a pressure-resistant built-in door 35 disposed on the pressure-resistant based on first implementation mode to the eighth implementation mode. The high/low-pressure forming apparatus 1 includes a movement apparatus 4, a pressure forming rod 2, a pressure forming body 7, a pressure forming shell 6 and a valve, where the valve includes a pressure suction valve and a pressurization valve, and the high/low-pressure forming apparatus 1 is a device for manufacturing a high-pressure space or a low-pressure space. The high/low-pressure control valve 59 of the present disclosure includes a valve shell 73, a valve body 66 and a valve deck 61.

A pressurizing port 62 (A), a pressure reduction port 68 (B), an air evacuation port 71 (D), an air filling port 68 (C), a circulating air inlet 63 (E) and a circulating air outlet 70 (F) are disposed on the valve shell 73. A three-way hole 64, a circulating air intake hole 74 and a circulating air vent hole 75 are disposed on the valve body 66.

The variable-pressure dish-washing machine of the present disclosure includes a pressure-resistant shell 39, a built-in groove 36, a pressure-resistant sealing apparatus 80, a pressure regulating valve 37, a pressure-resistant built-in door 35, an inspection window 38, a tableware 53 and a tableware rack 54. A high/low-pressure forming apparatus 1 is disposed on the variable-pressure dish-washing machine and includes a movement apparatus, a pressure forming rod 2, a pressure forming body 7, a pressure forming shell 6 and a valve. The valve includes a pressure suction valve 11 and a pressurization valve 15. The high/low-pressure forming apparatus 1 is a device for manufacturing a high-pressure compartment or a low-pressure compartment.

Implementation Mode 10

A pickling machine is shown in FIGS. 1 to 3, 8 and 10 to 12. In this implementation mode based on first implementation mode to the ninth implementation mode, an inner side of a pressure-resistant shell 39 of a pickling machine forms a high-pressure compartment or a low-pressure compartment through a high/low-pressure forming apparatus 1, a high/low-pressure control valve 59 and a pressure-resistant built-in door 35 disposed on the pressure-resistant shell 39. The high/low-pressure forming apparatus 1 includes a movement apparatus 4, a pressure forming rod 2, a pressure forming body 7, a pressure forming shell 6 and a valve, where the valve includes a pressure suction valve and a pressurization valve, and the high/low-pressure forming apparatus 1 is a device for manufacturing a high-pressure space or a low-pressure space. The high/low-pressure control valve 59 of the present disclosure includes a valve shell 73, a valve body 66 and a valve deck 61.

A pressurizing port 62 (A), a pressure reduction port 68 (B), an air evacuation port 71 (D), an air filling port 68 (C), a circulating air inlet 63 (E) and a circulating air outlet 70 (F) are disposed on the valve shell 73. A three-way hole 64, a circulating air intake hole 74 and a circulating air vent hole 75 are disposed on the valve body 66.

The pickling machine of the present disclosure includes a pressure-resistant shell 39, a built-in groove 36, a pressure-resistant sealing apparatus 80, a pressure regulating valve 37, a pressure-resistant built-in door 35, an inspection window 38, a tableware 53, a tableware rack 54 and food 55. A high/low-pressure forming apparatus 1 is disposed on the pickling machine and includes a movement apparatus, a pressure forming rod 2, a pressure forming body 7, a pressure forming shell 6 and a valve. The valve includes a pressure suction valve 11 and a pressurization valve 15. The high/low-pressure forming apparatus 1 is a device for manufacturing a high-pressure space or a low-pressure space.

Implementation Mode 10

A footwear foot-care machine is shown in FIGS. 1 to 3, 9 and FIGS. 10 to 12. In this implementation mode, an inner side of a pressure-resistant shell 39 of the footwear foot-care machine forms a high-pressure compartment or a low-pressure compartment through a high/low-pressure forming apparatus 1, a high/low-pressure control valve 59 and a pressure-resistant built-in door 35 disposed on the pressure-resistant shell 39 disposed on the pressure-resistant shell 39. The high/low-pressure forming apparatus of the present disclosure 1 includes a movement apparatus 4, a pressure forming rod 2, a pressure forming body 7, a pressure forming shell 6 and a valve, where the valve includes a pressure suction valve and a pressurization valve, and the high/low-pressure forming apparatus 1 is a device for manufacturing a high-pressure space or a low-pressure space. The high/low-pressure control valve 59 of the present disclosure includes a valve shell 73, a valve body 66 and a valve deck 61.

A pressurizing port 62 (A), a pressure reduction port 68 (B), an air evacuation port 71 (D), an air filling port 68 (C), a circulating air inlet 63 (E) and a circulating air outlet 70 (F) are disposed on the valve shell 73. A three-way hole 64, a circulating air intake hole 74 and a circulating air vent hole 75 are disposed on the valve body 66.

The footwear foot-care machine includes a pressure-resistant 39, a footwear chamber is disposed in the pressure-resistant shell 39 and is provided with a build-in groove 36, a pressure-resistant sealing apparatus 80, a pressure regulating groove 37, a pressure-resistant build-in door 35 and an inspection window 38. A pressurization valve and a breather valve are disposed on the footwear chamber, and a footwear rack 57 is disposed in the footwear chamber to place a footwear 58; or a vibration apparatus 48 is disposed in the footwear chamber and is integrally provided with or coupled with the footwear rack 57, and the footwear 58 is placed on the footwear rack 57 or the vibration apparatus 48. Air is discharged from the footwear chamber by the pressure suction valve to form a low pressure, and the sweat stain odor expands and decomposes under the low pressure and then is discharged from the footwear chamber by a safety valve 32, or is treated by a deodorization purifying agent, vibrated by the vibration apparatus 48 and then discharged by the pressure suction valve to form a low pressure. After continuous low-pressure treatment, air is discharged by the safety valve 32 to be a normal pressure state, and the footwear 58 is then taken out.

According to the above structure, since multiple pressure forming shells 6 are, in a combination or integrally, disposed on the high/low-pressure forming apparatus, a high-pressure or low-pressure environment is formed more efficiently. Multiple pressure forming shells 6 are disposed on the high/low-pressure forming apparatus 1, an inner side of each pressure forming shell 6 is provided with one pressure forming body 7, and an outer periphery of the bottom of each pressure forming shell 6 and a bottom cover is integrally provided or coupled together. The outer periphery of the bottom of the pressure forming shell 6 is integrally provided with or coupled with the pressure suction valve 11 or the pressurization valve 15, the pressure forming body 7 reciprocates in the each pressure forming shell 6 to enlarge or reduce the space in the pressure forming shell 6, so that the pressure in the pressure forming shell 6 is increased or decreased by several times, and the pressurization valve 15 or the pressure suction valve 11 in different coupling manners acts on a compartment of an external device to form a high-pressure space in which the pressure is larger than the atmospheric pressure or a low-pressure space in which the pressure is lower than the atmospheric pressure. The technology of manufacturing the high-pressure space or the low-pressure space can be implemented in the refrigerator, the washing machine, the dish-washing machine, a pickling machine, a floor washing machine, a clothes processing machine and other household electric appliances, so that mold and peculiar smell can be expelled, bacteria or other harmful components adhered to food can be effectively removed. In addition, the high-pressure pickling can shorten the processing time, the nutrient loss is avoided, the high-pressure pickling is very convenient, the efficiency is improved and the harm of food deterioration to human health is prevented.

Although the above description is given by taking the use of 1 the high/low-pressure forming apparatus, 2 the safety door, and 3 the high/low-pressure control valve on a refrigerator, a clothes processing machine, a variable-pressure dish-washing machine, a pickling machine and a footwear foot-care machine as an example, 1 the high/low pressure forming apparatus, 2 the safety door and 3 the high/low-pressure control valve of the present disclosure can also be implemented in more manners. 1 The high/low-pressure forming apparatus, 2 the safety door and 3 the high/low-pressure control valve of the present disclosure can also have more structural manners. In the above-mentioned structure, the structure of the described embodiments and any other combination can be adopted, or the disclosure can be used on other devices.

The preferred embodiments described above are illustrative rather than limiting, and the present disclosure may be implemented and embodied in other ways without departing from the spirit and essential features of the present disclosure.

The scope of the present disclosure is defined by the claims, and all variations within the scope defined by the claims fall within the scope of the present disclosure.

What is claimed is:

1. A household electric appliance with a high-low pressure function, comprising a high-low pressure forming apparatus, wherein the high-low pressure forming apparatus comprises a movement apparatus, a pressure forming rod, a pressure forming body, a pressure forming shell and a valve, wherein the valve comprises a pressure suction valve and a pressurization valve, and the high-low pressure forming apparatus is a device for manufacturing a high-pressure compartment or a low-pressure compartment of the household electric appliance with the high-low pressure function;

wherein an outer periphery of a bottom of the pressure forming shell of the high-low pressure forming apparatus is integrally provided with or coupled with the pressurization valve for manufacturing a pressure higher than an atmospheric pressure and the pressure suction valve for manufacturing a pressure lower than the atmospheric pressure;

wherein the high-low pressure forming apparatus is integrally provided with or coupled with the household electric appliance with the high-low pressure function, and the pressure forming shell is integrally provided with or coupled with the high-low pressure forming apparatus, wherein an inner side of the pressure forming shell is provided with the pressure forming body which reciprocates axially along a hole wall in the pressure forming shell, the pressure forming body is integrally provided with or coupled with the pressure forming rod in a movable fit manner, the other end of the one pressure forming rod is integrally provided with or coupled with a transmission apparatus in a movable fit manner, and the transmission apparatus is integrally provided with or coupled with a power apparatus; and wherein when the pressure forming body axially reciprocates along the hole wall in the pressure forming shell to a position where space between the pressure forming body in the pressure forming shell and a bottom cover of the pressure forming shell reaches the maximum and contains maximum amount of gas, the pressure forming body compresses space of internal gas to form a high pressure, or when the pressure forming body axially reciprocates along the hole wall in the pressure forming shell to a position where space between the pressure forming body in the pressure forming shell and a bottom cover of the pressure forming shell reaches the minimum and contains minimum amount of gas, the pressure forming body expands space of internal gas to form a low pressure.

2. A household electric appliance with a high-low pressure function, comprising a pressure-resistant apparatus and a safety door, wherein a high-pressure compartment or a low-pressure compartment is formed in a pressure-resistant shell of the household electric appliance with the high-low pressure function through adjusting a high-pressure gas or a low-pressure gas generated by a high-low pressure forming apparatus of the household electric appliance via a high-low pressure control valve, wherein the pressure-resistant shell is provided with a built-in groove, a sealing apparatus and a pressure-resistant built-in door;

wherein the pressure-resistant shell is disposed on the household electric appliance with the high-low pressure function;

wherein the built-in groove is integrally provided on or coupled on an inner side of the pressure-resistant shell, a pressure-resistant sealing apparatus is disposed in the built-in groove, and the pressure-resistant built-in door is disposed in the built-in groove via the pressure-resistant sealing apparatus; and wherein an outer end of a side of the built-in groove is integrally provided with an opening on the pressure-resistant shell, and the pressure-resistant built-in door is completely pushed into a sealing state in the built-in groove via the opening of the pressure-resistant shell, and the pressure-resistant shell forms the high-pressure compartment or the low-pressure compartment through a pressurization apparatus or a pressure suction apparatus; or wherein the pressure-resistant built-in door continues to move outward along a groove-shaped opening in the built-in groove to an open state to take out articles in the pressure-resistant shell, that is, the high-pressure compartment or the low-pressure compartment.

3. A household electric appliance with a high-low pressure function, comprising a high-low pressure control valve on a high-pressure compartment or a low-pressure compartment of the household electric appliance with the high-low pressure function, wherein the high-low pressure control valve comprises a valve shell, a valve body and a valve deck; wherein the high-pressure compartment or the low-pressure compartment of the household electric appliance with the high-low pressure function is integrally provided with or coupled with a high-low pressure forming apparatus via the high-low pressure control valve, and the high-low pressure control valve comprises the valve shell, the valve body and the valve deck;

wherein the valve shell is provided with a pressurization port, a pressure reduction port, an air filling port, an air evacuation port, a circulating air inlet and a circulating air outlet;

wherein the valve body is provided with a three-way hole, a circulating air intake hole and a circulating air vent hole;

wherein an upper part of the valve body is integrally provided with or coupled with a valve handle, the valve handle is coupled with a transmission apparatus, and the three-way hole cooperates with the pressurization port, the air filling port, the pressure reduction port and the air evacuation port to form a closing or opening fit for a high pressure or a low pressure; and wherein the circulating air intake hole cooperates with the pressurization port via the circulating air inlet, or the circulating air vent hole cooperates with the pressure reduction port via the circulating air outlet.

4. The household electric appliance with the high-low pressure function of claim 1, wherein a plurality of pressure forming shells are integrally disposed on or coupled on the household electric appliance with the high-low pressure function; and each of the plurality of pressure forming shells is integrally provided with or coupled with two pressure forming bodies which reciprocate axially along a hole wall in the each of the plurality of pressure forming shells, each of the two pressure forming bodies is integrally provided with or coupled with one pressure forming rod in a movable fit manner, the two pressure forming rods are integrally provided with or coupled with one eccentric gear or one eccentric rod in a movable fit manner, and the one eccentric gear or the one eccentric rod is integrally provided with or coupled with the power apparatus via the transmission apparatus.

5. The household electric appliance with the high-low pressure function of claim 1, wherein an outer periphery of a bottom of the pressure forming shell of the high-low pressure forming apparatus of the household electric appliance with the high-low pressure function is integrally provided with or coupled with the pressure suction valve and the pressurization valve, a rotating apparatus of the pressure suction valve and a rotating apparatus of the pressurization valve are intercoupled via the transmission apparatus and then are integrally provided with or coupled with the power apparatus, the rotating handles are driven by the rotating apparatuses of the pressure suction valve and the pressurization valve to rotate and drive rotation reverse of the pressure suction valve rotating body and the pressurization valve rotating body so as to change a movement direction of an airflow, thereby switching a flow direction of a suctioning or outputting gas or fluid for the high pressure or the low pressure in a compartment of an external device coupled with the high-low pressure apparatus.

6. The household electric appliance with the high-low pressure function of claim 1, wherein a rotating apparatus disposed on the pressure suction valve rotating handle and a rotating apparatus disposed on the pressurization valve rotating handle of the high-low pressure forming apparatus of the household electric appliance with the high-low pressure function are integrally provided or coupled via the transmission apparatus.

7. The high-low pressure forming apparatus of claim 1, wherein the pressure suction valve of the high-low pressure forming apparatus is integrally provided with or coupled with the low-pressure compartment of the household electric appliance with the high-low pressure function via the high-low pressure control valve, or the pressurization valve of the high-low pressure forming apparatus is integrally provided with or coupled with the high-pressure compartment of the household electric appliance.

8. The household electric appliance with the high-low pressure function of claim 1, wherein the high-low pressure forming apparatus is disposed on the household electric appliance with the high-low pressure function, and at least two pressure forming shells are integrally disposed on or coupled on the high-low pressure forming apparatus;

wherein an inner side of each of the at least two pressure forming shells is provided with one pressure forming body which reciprocates axially along a hole wall in the each of the at least two pressure forming shells, each pressure forming body is integrally provided with or coupled with one pressure forming rod in a movable fit manner, the other ends of the at least two pressure forming rods are each integrally provided with or coupled with a transmission apparatus in a movable fit manner, and the transmission apparatus is integrally provided with or coupled with a power apparatus;

wherein when the one pressure forming body axially reciprocates along the hole wall in the each of the at least two pressure forming shells reciprocates to a position where space between the one pressure forming body in the each of the at least two pressure forming shells and a bottom cover of the each of the at least two pressure forming shells reaches the maximum and contains maximum amount of gas, the one pressure forming body compresses space of internal gas to form a high pressure, or when the one pressure forming body axially reciprocates along the hole wall in the each of the at least two pressure forming shells reciprocates to a position where space between the one pressure forming body in the each of the at least two pressure forming shells and a bottom cover of the each of the at least two pressure forming shells reaches the minimum and contains minimum amount of gas, the one pressure forming body expands space of internal gas to form a low-pressure; and wherein an outer periphery of a bottom of each of the at least two pressure forming shells of the high-low pressure forming apparatus is integrally provided with or coupled with the pressurization valve for manufacturing a pressure higher than an atmospheric pressure and the pressure suction valve for manufacturing a pressure lower than the atmospheric pressure.

9. The household electric appliance with the high-low pressure function of claim 1, wherein the high-low pressure forming apparatus is integrally provided with or coupled with the pressurization valve for manufacturing a pressure higher than an atmospheric pressure and the pressure suction valve for manufacturing a pressure lower than the atmospheric pressure;

wherein a cavity of the pressure suction valve is integrally provided with or coupled with a pressure suction valve rotating body in a movable fit manner, a check valve is disposed in the pressure suction valve rotating body, the pressure suction valve rotating body is integrally provided in or coupled in the cavity of the pressure suction valve in a movable fit manner, a cavity of the pressurization valve is integrally provided with or coupled with a pressurization valve rotating body in a movable fit manner, a check valve is disposed in the pressurization valve rotating body, and the pressurization valve rotating body is integrally provided in or coupled in the cavity of the pressurization valve in the movable fit manner; and wherein a top end of each of the pressure suction valve rotating body and the pressurization valve rotating body is integrally provided with or coupled with a rotating handle, and the rotating handle is integrally provided with or coupled with a rotating apparatus.

10. The household electric appliance with the high-low pressure function of claim 1, wherein a cavity of the pressure suction valve of the high-low pressure forming apparatus of the household electric appliance with the high-low pressure function is integrally provided with or coupled with a pressure suction valve rotating body in a movable fit manner, a check valve is disposed in the pressure suction valve rotating body, the pressure suction valve rotating body is integrally provided in or coupled in the cavity of the pressure suction valve in the movable fit manner;

wherein a cavity of the pressurization valve is integrally provided with or coupled with a pressurization valve rotating body in a movable fit manner, a check valve is disposed in the pressurization valve rotating body, and the pressurization valve rotating body is integrally provided in or coupled in the cavity of the pressurization valve in the movable fit manner; and wherein a top end of each of the pressure suction valve rotating body and the pressurization valve rotating body is integrally provided with or coupled with a rotating handle, and the rotating handle is integrally provided with or coupled with a rotating apparatus.

11. The household electric appliance with the high-low pressure function of claim 2, wherein a plurality of pressure forming shells are integrally disposed on or coupled on the household electric appliance with the high-low pressure function; and each of the plurality of pressure forming shells is integrally provided with or coupled with two pressure forming bodies which reciprocate axially along a hole wall in the each of the plurality of pressure forming shells, each of the two pressure forming bodies is integrally provided with or coupled with one pressure forming rod in a movable fit manner, the two pressure forming rods are integrally provided with or coupled with one eccentric gear or one eccentric rod in a movable fit manner, and the one eccentric gear or the one eccentric rod is integrally provided with or coupled with the power apparatus via the transmission apparatus.

12. The household electric appliance with the high-low pressure function of claim 3, wherein a plurality of pressure forming shells are integrally disposed on or coupled on the household electric appliance with the high-low pressure function; and each of the plurality of pressure forming shells is integrally provided with or coupled with two pressure forming bodies which reciprocate axially along a hole wall in the each of the plurality of pressure forming shells, each of the two pressure forming bodies is integrally provided with or coupled with one pressure forming rod in a movable fit manner, the two pressure forming rods are integrally provided with or coupled with one eccentric gear or one eccentric rod in a movable fit manner, and the one eccentric gear or the one eccentric rod is integrally provided with or coupled with the power apparatus via the transmission apparatus.

13. The household electric appliance with the high-low pressure function of claim 8, wherein a plurality of pressure forming shells are integrally disposed on or coupled on the household electric appliance with the high-low pressure function; and each of the plurality of pressure forming shells is integrally provided with or coupled with two pressure forming bodies which reciprocate axially along a hole wall in the each of the plurality of pressure forming shells, each of the two pressure forming bodies is integrally provided with or coupled with one pressure forming rod in a movable fit manner, the two pressure forming rods are integrally provided with or coupled with one eccentric gear or one eccentric rod in a movable fit manner, and the one eccentric gear or the one eccentric rod is integrally provided with or coupled with the power apparatus via the transmission apparatus.

14. The household electric appliance with the high-low pressure function of claim 2, wherein an outer periphery of a bottom of the pressure forming shell of the high-low pressure forming apparatus of the household electric appliance with the high-low pressure function is integrally provided with or coupled with the pressure suction valve and the pressurization valve, a rotating apparatus of the pressure suction valve and a rotating apparatus of the pressurization valve are intercoupled via the transmission apparatus and then are integrally provided with or coupled with the power apparatus, the rotating handles are driven by the rotating apparatuses of the pressure suction valve and the pressurization valve to rotate and drive rotation reverse of the pressure suction valve rotating body and the pressurization valve rotating body so as to change a movement direction of an airflow, thereby switching a flow direction of a suctioning or outputting gas or fluid for the high pressure or the low pressure in a compartment of an external device coupled with the high-low pressure apparatus.

15. The household electric appliance with the high-low pressure function of claim 3, wherein an outer periphery of a bottom of the pressure forming shell of the high-low pressure forming apparatus of the household electric appliance with the high-low pressure function is integrally provided with or coupled with the pressure suction valve and the pressurization valve, a rotating apparatus of the pressure suction valve and a rotating apparatus of the pressurization valve are intercoupled via the transmission apparatus and then are integrally provided with or coupled with the power apparatus, the rotating handles are driven by the rotating apparatuses of the pressure suction valve and the pressurization valve to rotate and drive rotation reverse of the pressure suction valve rotating body and the pressurization valve rotating body so as to change a movement direction of an airflow, thereby switching a flow direction of a suctioning or outputting gas or fluid for the high pressure or the low pressure in a compartment of an external device coupled with the high-low pressure apparatus.

16. The household electric appliance with the high-low pressure function of claim 8 wherein an outer periphery of a bottom of the pressure forming shell of the high-low pressure forming apparatus of the household electric appliance with the high-low pressure function is integrally provided with or coupled with the pressure suction valve and the pressurization valve, a rotating apparatus of the pressure suction valve and a rotating apparatus of the pressurization valve are intercoupled via the transmission apparatus and then are integrally provided with or coupled with the power apparatus, the rotating handles are driven by the rotating apparatuses of the pressure suction valve and the pressurization valve to rotate and drive rotation reverse of the pressure suction valve rotating body and the pressurization valve rotating body so as to change a movement direction of an airflow, thereby switching a flow direction of a suctioning or outputting gas or fluid for the high pressure or the low pressure in a compartment of an external device coupled with the high-low pressure apparatus.

17. The household electric appliance with the high-low pressure function of claim 2, wherein a rotating apparatus disposed on the pressure suction valve rotating handle and a rotating apparatus disposed on the pressurization valve rotating handle of the high-low pressure forming apparatus of the household electric appliance with the high-low pressure function are integrally provided or coupled via the transmission apparatus.

* * * * *